United States Patent
Thye et al.

(10) Patent No.: US 9,629,861 B2
(45) Date of Patent: Apr. 25, 2017

(54) COMPOSITIONS AND METHODS FOR TREATING BACTERIAL INFECTIONS USING CEFTAROLINE

(71) Applicant: Forest Laboratories Holdings Limited, Hamilton (BM)

(72) Inventors: Dirk Thye, San Francisco, CA (US); George Talbot, Wayne, PA (US)

(73) Assignee: FOREST LABORATORIES HOLDING LIMITED, Hamilton (BM)

( * ) Notice: Subject to any disclaimer, the term of this patent is extended or adjusted under 35 U.S.C. 154(b) by 0 days.

(21) Appl. No.: 14/722,495

(22) Filed: May 27, 2015

(65) Prior Publication Data

US 2015/0258126 A1 Sep. 17, 2015

Related U.S. Application Data

(63) Continuation of application No. 12/887,140, filed on Sep. 21, 2010, now abandoned.

(60) Provisional application No. 61/244,120, filed on Sep. 21, 2009, provisional application No. 61/294,901, filed on Jan. 14, 2010.

(51) Int. Cl.
*A61K 31/675* (2006.01)
*A61K 9/00* (2006.01)
*A61K 47/18* (2017.01)

(52) U.S. Cl.
CPC .......... *A61K 31/675* (2013.01); *A61K 9/0019* (2013.01); *A61K 47/183* (2013.01)

(58) Field of Classification Search
CPC ... A61K 31/675; A61K 47/183; A61K 9/0019
See application file for complete search history.

(56) References Cited

U.S. PATENT DOCUMENTS

| | | | |
|---|---|---|---|
| 6,417,175 | B1 | 7/2002 | Ishikawa et al. |
| 6,906,055 | B2 | 6/2005 | Ishikawa et al. |
| 7,419,973 | B2 | 9/2008 | Ishikawa et al. |
| 2003/0186339 | A1 | 10/2003 | Leyland-Jones et al. |
| 2004/0023943 | A1* | 2/2004 | Ishikawa ............ C07F 9/65613 514/206 |
| 2009/0082326 | A1 | 3/2009 | Dedhiya et al. |

FOREIGN PATENT DOCUMENTS

WO    WO 03079972 A2 * 10/2003 ....... A61K 47/48246

OTHER PUBLICATIONS

Wang et. al., Drugs of the Future, 2008, Prous Science, vol. 33(4), pp. 302-309.*
Kanafani et. al., Future Microbiology, Feb. 2009, Future Medicine, vol. 4(1), pp. 25-33.*
Ge et al, Ceftaroline (CPT) Dose Adjustment Recommendations for Subjects with Mild or Moderate Renal mpairment (RI), ICAAC Poster A-35, 2007.
Ge, Y et al, Pharmacokinetics (PK) of Certaroline (PPI0903) in Subjects with Mild or Moderate Renal Impairment (RI), 46th Interscience Conference on Antimicrobial Agents and Chemotherapy, Sep. 27-30, 2006, 28-29, A-1939.
Kizler, T. Alp et al, Spontaneous Dietary Protein Intake During Progression of Chronic Renal Failure, Journal of the American Society of Nephrology, 1995, 1386-1391, 6.
Page, Michael et al, Mechanism of Beta-Lactam Ring OPening in Cephalosporins, J Am Chem Soc, 1984, 3820-3825, 106.
Riccobene et al, An Open-Label Pharmacokinetic (PK), Safety, and Tolerability Study of Single Intravenous (IV) Doses of Ceftaroline (CPT) in Subjects with Normal Renal Function or Severe Renal Impairment, ICAAC Poster A1-003, 2009.
Riccobene et al, An Open-Label, Pharmacokinetic, Safety and Tolerability Study of Single-Dose Intravenous Ceftaroline in Subjects with End-Stage Renal Disease on Intermittent Haemodialysis, ICAAC Poster P1455, 2009.
Talbot, George et al, Phase 2 Study of Certaroline Versus Standard Therapy in Treatment of Complicated Skin and Skin Structure Infections, Antimicrobial Agents and Chemotherapy, Oct. 2007, 3612-3616, 51(10).
Teflaro (ceftaroline fosamil) injection for intravenous (IV) use, Package Insert, 2010, 23 Pages.
Zhanel, George et al, Ceftaroline: A Novel Broad-Spectrum Cephalosporin with Activity Against Meticillin-Resistant *Staphylococcus aureus*, Drugs, 2009, 809-831, 69(7).

* cited by examiner

*Primary Examiner* — Sarah Pihonak
(74) *Attorney, Agent, or Firm* — Andrew Chien

(57) ABSTRACT

The present invention relates to compositions comprising ceftaroline or a prodrug thereof (e.g., ceftaroline fosamil) and methods for treating bacterial infections, such as complicated skin and structure infections (cSSSI) and community-acquired bacterial pneumonia (CABP) by administering ceftaroline or a prodrug thereof, (e.g., ceftaroline fosamil).

8 Claims, No Drawings

COMPOSITIONS AND METHODS FOR TREATING BACTERIAL INFECTIONS USING CEFTAROLINE

CROSS-REFERENCE TO RELATED APPLICATIONS

This application claims priority under 35 U.S.C. §119, based on U.S. Provisional Application Ser. No. 61/244,120 filed on Sep. 21, 2009 and U.S. Provisional Application Ser. No. 61/294,901 filed on Jan. 14, 2010, both of which are hereby incorporated by reference in their entirety.

FIELD OF THE INVENTION

The present invention relates to compositions comprising ceftaroline or a prodrug thereof (e.g., ceftaroline fosamil) and methods for treating bacterial infections, such as complicated skin and structure infections (cSSSI) and community-acquired bacterial pneumonia (CABP) by administering ceftaroline or a prodrug thereof (e.g., ceftaroline fosamil).

BACKGROUND OF THE INVENTION

Ceftaroline is a novel parenteral cephalosporin with a broad spectrum of activity against clinically important community-acquired and hospital-acquired Gram-negative and Gram-positive pathogens including methicillin-resistant *Staphylococcus aureus* and multidrug-resistant *Streptococcus pneumoniae*.

U.S. Pat. No. 6,417,175 discloses compounds having excellent antibacterial activities for a broad range of Gram-positive and Gram-negative bacteria. These compounds are represented by the general formula:

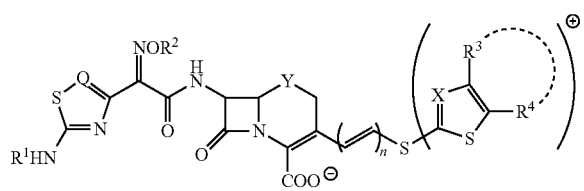

wherein $R^1$-$R^4$, Q, X, Y and n are as defined therein.

U.S. Pat. No. 6,417,175 discloses methods for preparing the compounds, and generically discloses formulations of the compounds, such as aqueous and saline solutions for injection. One such compound is 7β-[2(Z)-ethoxyimino-2-(5-phosphonoamino-1,2,4-thiadiazole-3-yl)acetamido]-3-[4-(1-methyl-4-pyridinio)-2-thiazolythio]-3-cephem-4-carboxylate.

U.S. Pat. No. 6,906,055 discloses a chemical genus which includes compounds of formula:

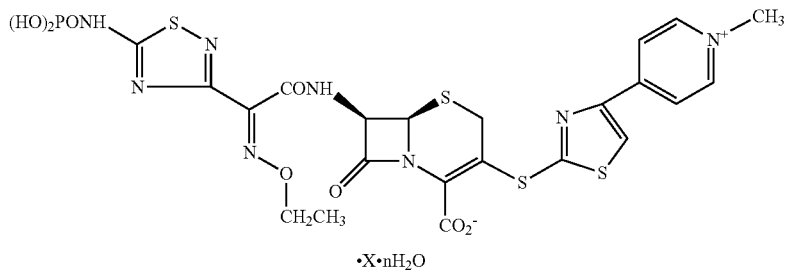

·X·nH₂O

Ceftaroline fosamil is a sterile, synthetic, parenteral pro-drug cephalosporin antibiotic. The N-phosphonoamino water-soluble prodrug is rapidly converted into the bioactive ceftaroline, which has been demonstrated to exhibit antibacterial activity. Ceftaroline fosamil is known as (6R,7R)-7-{(2Z)-2-(ethoxyimino)-2-[5-(phosphonoamino)-1,2,4-thiadiazol-3-yl]acetamido}-3-{[4-(1-methylpyridin-1-ium-4-yl)-1,3-thiazol-2-yl]sulfanyl}-8-oxo-5-thia-1-azabicyclo[4.2.0]oct-2-ene-2-carboxylate. Ceftaroline fosamil may be an acetic acid hydrous form.

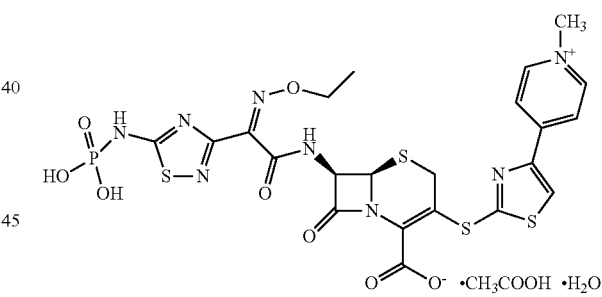

U.S. Pat. No. 7,419,973 discloses compositions comprising ceftaroline fosamil and a pH adjuster, such as, L-arginine.

U.S. Pat. Nos. 6,417,175 and 6,906,055 and 7,419,973 are incorporated herein by reference, in their entirety.

There is an existing and continual need in the art for new and improved compositions comprising ceftaroline or a prodrug thereof and methods for treating bacterial infections by administering ceftaroline or a prodrug thereof. The present invention provides compositions and methods for treating bacterial infections using ceftaroline or a prodrug thereof (e.g., ceftaroline fosamil). These compositions and methods are surprisingly and unexpectedly effective in treating bacterial infections, such as complicated skin and structure infections (cSSSI) and community-acquired bacterial pneumonia (CABP).

SUMMARY OF THE INVENTION

According to some embodiments, the present invention provides compositions for treatment of bacterial infections that comprise from about 200 mg to about 800 mg of ceftaroline or a prodrug thereof and less than 2% of an L-arginine adduct.

According to some embodiments, the present invention provides compositions for treatment of bacterial infections that comprise from about 200 mg to about 800 mg of ceftaroline or a prodrug thereof, and provide a mean AUC for ceftaroline in patients with a creatinine clearance from about 50 to about 80 ml/min of about 1.2 times greater than mean AUC for ceftaroline in patients with a creatinine clearance of more than about 80 ml/min.

According to some embodiments, the present invention provides compositions for treatment of bacterial infections that comprise from about 200 mg to about 800 mg of ceftaroline or a prodrug thereof and provide a mean AUC for ceftaroline in patients with a creatinine clearance from about 30 to about 50 ml/min of about 1.5 times greater than mean AUC for ceftaroline in patients with a creatinine clearance of more than about 80 ml/min.

According to some embodiments, the present invention provides methods for treating bacterial infections in patients in need thereof by providing a dosage form comprising about 200 mg to about 800 mg of ceftaroline or a prodrug thereof and adding about 20 ml of sterile water to the dosage form to form a constituted solution that has a pH of about 4.8 to about 6.5 and administering the constituted solution to the patients over a period of about one hour.

According to some embodiments, the present invention provides methods for treating bacterial infections by providing a dosage form comprising about 400 mg of ceftaroline or a prodrug thereof and administering a constituted solution comprising the dosage form over a period of about one hour to patients with a creatinine clearance from about 10 to about 50 ml/min.

According to some embodiments, the present invention provides methods for treating bacterial infections in patients in need thereof by providing a dosage form comprising about 600 mg of ceftaroline or a prodrug thereof and administering a constituted solution comprising the dosage form over a period of about one hour wherein the dosage form provides an in vivo plasma profile for ceftaroline comprising a Cmax of about 15 to about 30 µg/ml and an AUC of about 45 to about 75 µg h/ml.

According to some embodiments, the present invention provides methods for treating bacterial infections in patients in need thereof by providing a dosage form comprising about 600 mg of ceftaroline or a prodrug thereof and administering a constituted solution comprising the dosage form over a period of about one hour and repeating the administration every 12 hours over a period of about 5 to about 14 days.

According to some embodiments, the present invention provides methods for treating bacterial infections by providing a dosage form comprising about 400 mg of ceftaroline or a prodrug thereof and administering a constituted solution comprising the dosage form over a period of about one hour to patients with a creatinine clearance from about 10 to about 50 ml/min and repeating the administration every 12 hours over a period of about 5 to about 14 days.

According to some embodiments, the present invention provides methods for treating bacterial infections in patients in need thereof by administering a dosage form comprising about 200 mg to about 800 mg ceftaroline or a prodrug thereof and informing the patients that the composition is contraindicated in patients with known serious hypersensitivity or in patients who have demonstrated anaphylactic reactions to beta-lactams.

DETAILED DESCRIPTION OF THE INVENTION

The present invention relates to compositions comprising ceftaroline or a prodrug thereof and methods for treating bacterial infections by administering ceftaroline or a prodrug thereof.

In one aspect, the present invention provides compositions comprising ceftaroline or a prodrug thereof that are effective for the treatment of bacterial infections, e.g., complicated skin and structure infections (cSSSI) and community-acquired bacterial pneumonia (CABP). In some embodiments, the compositions comprise ceftaroline. In other embodiments, the compositions comprise phosphonocephem prodrugs of ceftaroline, e.g., ceftaroline fosamil. In exemplary embodiments, the ceftaroline fosamil is anhydrous. In other embodiments, the compositions comprise ceftaroline fosamil monohydrate acetic acid solvate.

In some embodiments, the compositions may comprise from about 100 mg to about 1200 mg of ceftaroline or a prodrug thereof (e.g., ceftaroline fosamil or ceftaroline fosamil monoacetate monohydrate). For example, the compositions may comprise about 100 mg, about 200 mg, about 300 mg, about 400 mg, about 500 mg, about 600 mg, about 800 mg, about 1000 mg, or about 1200 mg of ceftaroline or a prodrug thereof.

In some embodiments, the compositions comprise an amount of ceftaroline or prodrug thereof, which is effective for treatment of bacterial infections such as complicated skin and skin structure infections (cSSSI) and community-acquired bacterial pneumonia (CABP). The amount may be about 100 mg, about 200 mg, about 300 mg, about 400 mg, about 500 mg, about 600 mg, about 700 mg, about 800 mg, about 900 mg, about 1000 mg or about 1200 mg. In some examples, the amount may between about 200 mg to about 800 mg. In exemplary embodiments, the amount may be about 400 mg. In other exemplary embodiments, the amount may be about 600 mg. The compositions may further comprise one or more pharmaceutically acceptable carriers.

In further embodiments, the compositions may comprise L-arginine. L-arginine may be added as an alkalizing agent to control pH of the composition, to increase ionic strength and/or to improve solubility of ceftaroline or a prodrug thereof. For example, L-arginine may be added to control pH of a constituted solution comprising ceftaroline or a prodrug thereof to a pH between, about 4 and 7, for example, to a pH of about 4.8 to 6.5. In some examples, the pH may be between 4.5 and 6.5. Ceftaroline fosamil has aqueous solubility of about 8 to 30 mg per ml, which may be sufficient for some parenteral administration. L-arginine can improve the solubility to more than 200 mg per ml depending on the molarity of the solution. Thus, high doses, e.g., about 600 mg of ceftaroline fosamil can administered with a smaller amount of injectable fluid, e.g., about 2 ml or about 3 ml for intramuscular administration and using about 50 ml for infusion solution.

The ratio of ceftaroline or a prodrug thereof (e.g., ceftaroline fosamil or ceftaroline fosamil monoacetate monohydrate) to L-arginine may be about 1 to about 2, such as, about 1.4, about 1.5, about 1.6 or about 1.7. For example, the ratio may be about 1.5. In exemplary embodiments, the amount of L-arginine required to achieve the target pH in constituted solution may be about 660 mg/g of ceftaroline fosamil (anhydrous and acetic acid free), equivalent to ceftaroline fosamil:L-arginine (w/w) ratio of 1.5.

For example, about 395 mg of L-arginine may be used for about 600 mg of anhydrous and acetic acid free ceftaroline fosamil. In other examples, about 263 mg of L-arginine may be used for about 400 mg of anhydrous and acetic acid free ceftaroline fosamil. The ratio between ceftaroline fosamil monohydrate acetic acid solvate to L-arginine may be between about 1.7 to about 1.8.

Arginine can react with ceftaroline fosamil and its active metabolite ceftaroline to form an arginine adduct. The arginine adduct lacks beta-lactam ring and therefore, does not have antimicrobial properties. Thus, this reaction between ceftaroline and arginine is not desirable. The present invention provides new and improved compositions comprising ceftaroline or a prodrug thereof (e.g., ceftaroline fosamil) and L-arginine that comprise less than about 2% of arginine adduct. In some examples, the compositions comprise about 100 mg to about 1200 mg ceftaroline or a prodrug thereof (e.g., ceftaroline fosamil) and L-arginine and less than about 2% of arginine adduct. Such compositions are effective for the treatment of bacterial infections, e.g., cSSSI and CABP.

In some embodiments, the compositions may comprise an arginine adduct of Formula (I):

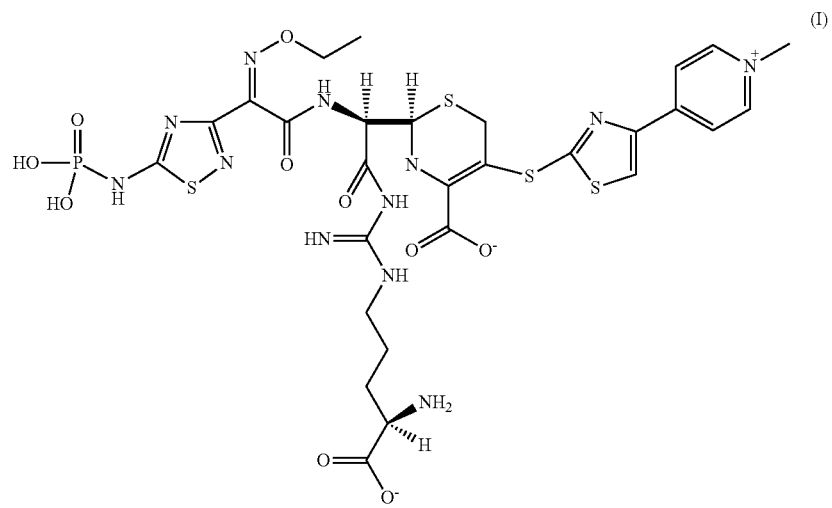

In other embodiments, the compositions may comprise an arginine adduct of Formula (II):

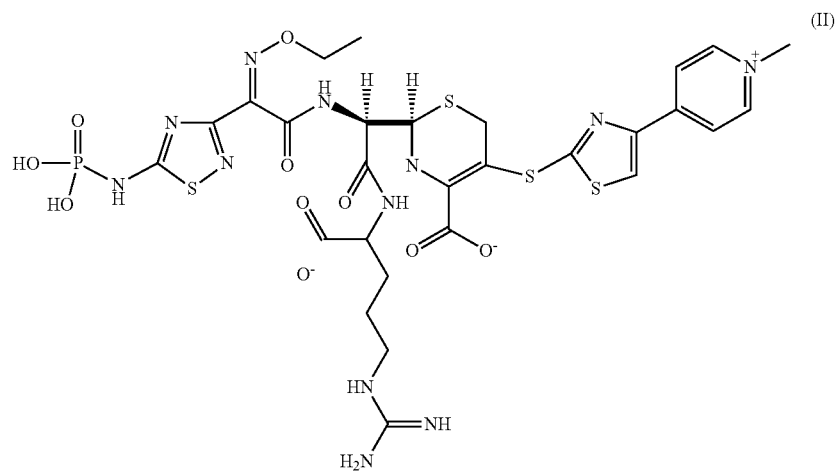

In some embodiments, the compositions comprise less than about 2% of arginine adduct. In exemplary embodiments, the compositions comprise from about 200 mg to about 800 mg of the ceftaroline or prodrug thereof, and less than about 2% of arginine adduct. In other exemplary embodiments, the compositions may comprise less than about 1.5% of arginine adduct, e.g., at a level below about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4% or about 1.5%. In exemplary embodiments, the compositions may comprise between about 0.01 to about 1.5% arginine adduct.

In some embodiments, the compositions may comprise less than about 10% total impurities. The impurities include, but are not limited to, process impurities or degradants of ceftaroline or a prodrug thereof. Some examples of such impurities are listed below.

U1 refers to ring opened ceftaroline of Formula (III):

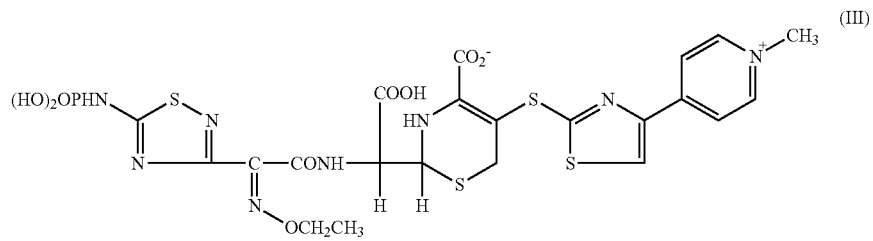

U2 refers to diphosphoric-type ceftaroline of Formula (IV):

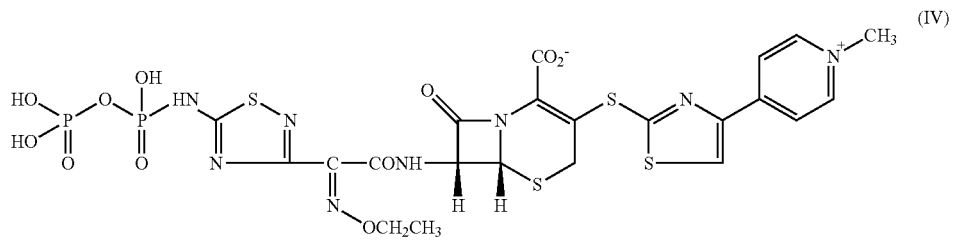

U3 refers to ceftaroline (active metabolite) of Formula (V):

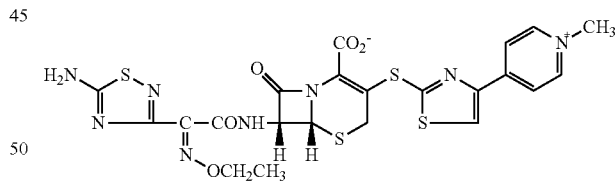

U4 refers to dimer of ceftaroline acetate of Formula (VI):

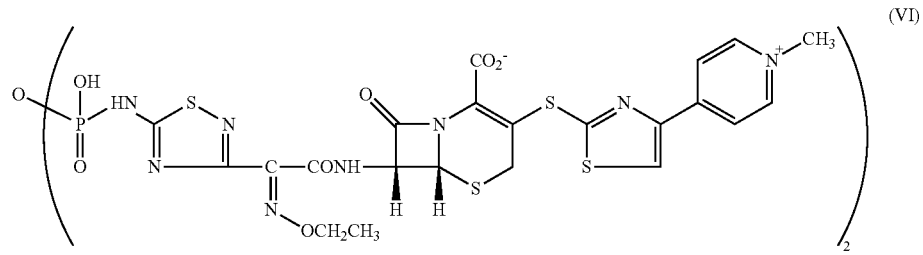

U5 refers to delta 2-type ceftaroline acetate of Formula (VII):
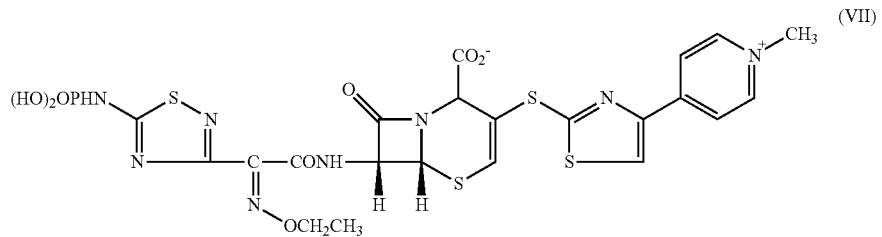
U6 refers to a ring-opened ceftaroline of Formula (VIII):
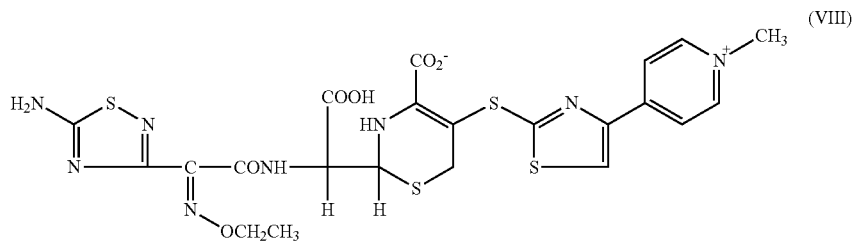
U7 referes to amide-type U-1 of Formula (IX):
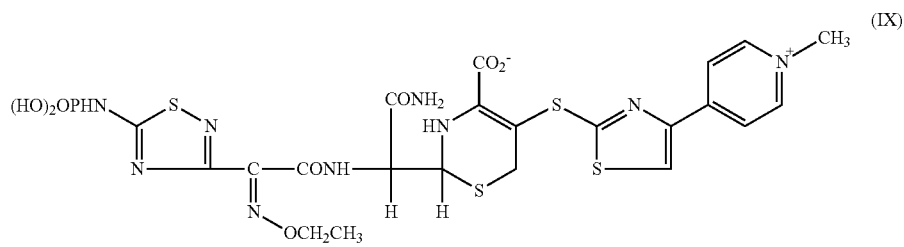
U8 refers to des-methyl-type ceftaroline acetate of Formula X:
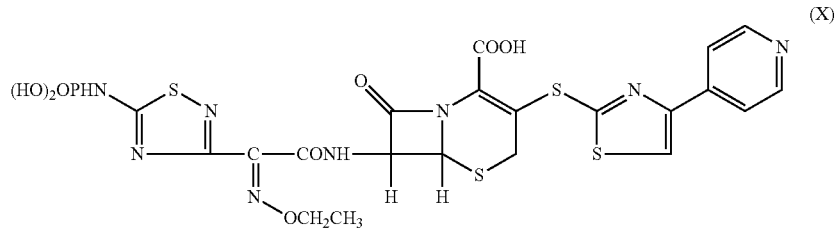
U9 refers to acetyl-type ceftaroline acetate of Formula XI:
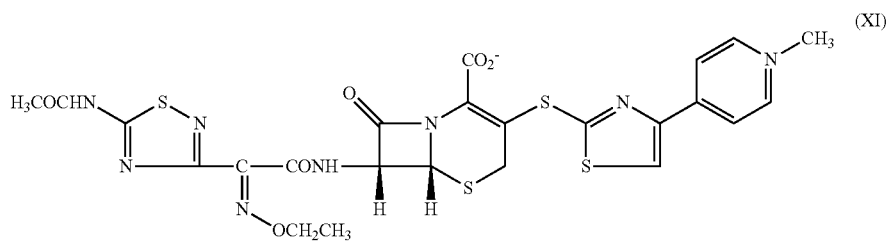

In some embodiments, the compositions comprise ceftaroline or a prodrug thereof (e.g., ceftaroline fosamil) and about 1 to 10% of impurities. In specific embodiments, the compositions may comprise about 0.05 to about 10% of impurities.

In exemplary embodiments, the compositions may comprise less than about 5% of impurities. For example, the compositions may comprise less than about 0.6% U1; less than about 0.6% U2, less than about 5% U3, less than about 0.2% U4, less than about 0.2% U5, less than about 0.6% U6, less than about 0.2% U7, less than about 0.2% U8, less than about 1% U9, or less than about 1.5% adducts.

In some embodiments, the compositions comprise about 0.05 to about 0.2% of U4, U5, U7 or U8. In other embodiments, the compositions comprise about 0.05 to about 0.6% of U1, U2 or U6. In still other embodiments, the compositions comprise about 0.05 to about 0.6% of U9. In certain embodiments, the compositions comprise about 0.05 to about 5% of U3. In other embodiments, the compositions comprise about 0.05 to about 1.5% of adduct.

Thus, in some embodiments the present invention provides compositions comprising ceftaroline or a prodrug thereof (e.g., ceftaroline fosamil) that are surprisingly and unexpectedly stable. For example, the compositions may include formulations comprising ceftaroline or a prodrug thereof (e.g., ceftaroline fosamil) and 0.9% sodium chloride, 5% dextrose, 2.5% dextrose, 0.45% sodium chloride or lactated Ringer's solution. In some embodiments, the compositions comprising ceftaroline or a prodrug thereof (e.g., ceftaroline fosamil) may include 0.9% sodium chloride and be surprisingly and unexpectedly stable as demonstrated by the level of one or more impurities or adducts.

The compositions comprising ceftaroline or a prodrug thereof may provide an in vivo plasma profile for ceftaroline comprising a Cmax of about 1 to about 100 μg/ml and an AUC of about 5 to about 200 μg h/ml. In specific embodiments, the compositions may provide an in vivo plasma profile for ceftaroline comprising a Cmax of about 2 to about 50 μg/ml and an AUC of about 5 to about 150 μg h/ml. For example, compositions comprising about 600 mg of ceftaroline or prodrug thereof may provide in vivo plasma profile for ceftaroline comprising a Cmax of about 15 to about 30 μg/ml and an AUC of about 45 to about 75 μg h/ml. In another example, compositions comprising about 400 mg of ceftaroline or a prodrug thereof may provide in vivo plasma profile for ceftaroline comprising a Cmax of about 8 to about 20 μg/ml and an AUC of about 25 to about 50 μg h/ml.

In some embodiments, the compositions comprise about 200 mg to 1200 mg ceftaroline fosamil and provide an in vivo plasma profile for ceftaroline comprising a mean Cmax of less than about 100 ug/ml. For example, the plasma profile comprises a mean Cmax of less than about 80 ug/ml; about 70 ug/ml; about 60 ug/ml; about 50 ug/ml; about 40 ug/ml or about 30 ug/ml. In exemplary embodiments, the plasma profile comprises a mean Cmax of about 10 to about 50 ug/ml. In other embodiments, the plasma profile comprises a mean Cmax of about 10 to about 40 ug/ml.

In other embodiments, the compositions comprise about 100 mg to 1200 mg ceftaroline fosamil and provide an in vivo plasma profile for ceftaroline comprising a mean $AUC_{0-\infty}$, of about 10 to 500 ug h/ml; about 10 to 400 ug h/ml ug h/ml; about 10 to 300 ug h/ml; about 10 to 200 ug h/ml or about 10 to 100 ug h/ml. In exemplary embodiments, the plasma profile comprises a mean $AUC_{0-\infty}$ of about 10 to 200 ug h/ml.

In exemplary embodiments, the compositions comprise from about 200 mg to about 800 mg of ceftaroline or a prodrug thereof and provide a mean AUC for ceftaroline in patients with a creatinine clearance from about 50 to about 80 ml/min, which is greater than mean AUC for ceftaroline in patients with a creatinine clearance of greater than about 80 ml/min. For example, the AUC may be up to about 2 times greater, e.g., about 1.2 times greater, about 1.3 times greater or about 1.5 times greater. In specific embodiments, the mean AUC for ceftaroline in patients with a creatinine clearance from about 50 to about 80 ml/min, is about 1.2 times greater than mean AUC for ceftaroline in patients with a creatinine clearance of greater than about 80 ml/min. For example, the compositions may comprise about 200 mg to 800 mg (such as about 600 mg) of ceftaroline or a prodrug thereof (such as ceftaroline fosamil) and provide a mean AUC for ceftaroline in patients with a creatinine clearance from about 50 to about 80 ml/min, which is about 10% to about 50% greater than mean AUC for ceftaroline in patients with a creatinine clearance of greater than about 80 ml/min. In some examples, the mean AUC may be increased by about 15%, about 16%, about 17%, about 18%, about 19%, about 20%, about 21%, about 22%, about 23%, about 24% or about 25%.

In other exemplary embodiments, the compositions comprise from about 200 mg to about 800 mg of ceftaroline or a prodrug thereof and provide a mean AUC for ceftaroline in patients with a creatinine clearance from about 30 to about 50 ml/min of up to about 3 times greater, such as about 1.5 times greater than mean AUC for ceftaroline in patients with a creatinine clearance of greater than about 80 ml/min. For example, the compositions may comprise about 200 to about 800 mg (such as about 600 mg) of ceftaroline or a prodrug thereof (such as ceftaroline fosamil) and provide a mean AUC for ceftaroline in patients with a creatinine clearance from about 30 to about 50 ml/min, which is about 40% to about 100% greater than mean AUC for ceftaroline in patients with a creatinine clearance of greater than about 80 ml/min. In some examples, the mean AUC may be increased by about 45%, about 46%, about 47%, about 48%, about 49%, about 50%, about 51%, about 52%, about 53%, about 54% or about 55%.

In some embodiments, the present invention provides compositions comprising about 200 mg to 1200 mg ceftaroline fosamil that provide an in vivo plasma profile for ceftaroline comprising a mean Tmax of more than about 10 min. For example, the plasma profile comprises a mean Tmax of more than about 15 minutes, 30 minutes, 45 minutes, 1 hour, 1.5 hours or about 2 hours. In exemplary embodiments, the plasma profile comprises a mean Tmax of about 30 minutes to about 4 hours, such as about 1.6 hours, about 2 hours, about 2.5 hours or about 3 hours.

In some embodiments, the present invention provides compositions consisting essentially of ceftaroline or a prodrug thereof (e.g., ceftaroline fosamil). In such compositions, ceftaroline or a prodrug thereof (e.g., ceftaroline fosamil) is the only active ingredient. An active ingredient as defined herein is one which is effective for the treatment of bacterial infections, e.g., an antibacterial agent or an antimicrobial agent. Such compositions can have other ingredients that are inactive and/or not antibacterial agents, antimicrobial agents. Examples of such ingredients include, but are not limited to, one or more pharmaceutically acceptable carriers, excipients, additives, or other ingredients useful in formulating the compositions.

Numerous standard references are available that describe procedures for preparing various compositions suitable for administering the compounds according to the invention. Examples of potential compositions and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

The compositions may be solid or liquid and be presented in the pharmaceutical forms, such as for example, plain or sugar-coated tablets, gelatin capsules, granules, suppositories, injectable preparations, ointments, creams, gels, and prepared according to the usual methods. The active ingredient or ingredients can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions may be presented in the form of a lyophilisate intended to be dissolved extemporaneously in an appropriate vehicle, e.g., apyrogenic sterile water. For example, the composition may be formulated as a solid dosage form, such as a dry powder, to be constituted with a diluent before administration. In exemplary embodiments, the composition may be formulated as a dry powder comprising ceftaroline or a prodrug thereof (e.g., ceftaroline fosamil). The dry powder may be constituted with a sterile diluent, such as water, to form a constituted solution before administration. The pH of the constituted solution may be between about 4 and about 7, for example, about 4.8 to about 6.5 or about 4.5 to about 6.5. In other embodiments, the pH of the constituted solution may be between about 5.6 and about 7. The constituted solution can be further diluted before administration using an appropriate solution, such as an infusion solution. Examples of such infusion solutions are 0.9% sodium chloride (normal saline), 5% dextrose, 2.5% dextrose and 0.45% sodium chloride and lactated Ringer's solution.

The compositions may be formulated in various solid oral dosage forms including such solid forms as tablets, gelcaps, capsules, caplets, granules, lozenges and bulk powders. The compositions of the present invention can be administered alone or combined with various pharmaceutically acceptable carriers, diluents (such as sucrose, mannitol, lactose, starches) and excipients known in the art, including, but not limited to suspending agents, solubilizers, buffering agents, binders, disintegrants, preservatives, colorants, flavorants, lubricants and the like. Time release capsules, tablets and gels may also be used in administering the compositions.

The compositions may also be formulated in various liquid oral dosage forms, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compositions of the present invention may be injected, for example, intravenously, in the form of an isotonic sterile solution. Other preparations are also possible.

For topical administration, the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, the compounds according to the invention can be administered by inhalation in the form of a powder (e.g., micronized) or in the form of atomized solutions or suspensions. The aerosol formulation can be placed into a pressurized acceptable propellant.

In another aspect, the present invention provides methods for treating bacterial infections by administering ceftaroline or a prodrug thereof. The methods include administering compositions or dosage forms comprising ceftaroline or a prodrug thereof as described above.

The methods include treatment of bacterial infections due to microorganisms, including Gram positive and Gram negative microorganisms such as *Staphylococcus aureus* (methicillin-susceptible and methicillin-resistant isolates), *Streptococcus pneumoniae* (including multidrug-resistant isolates [MDRSP]), *Streptococcus pyogenes, Streptococcus agalactiae, Streptococcus dysgalactiae, Streptococcus anginosus* group (including *S. anginosus, S. intermedius*, and *S. constellatus*), *Enterococcus faecalis* (ampicillin-susceptible), *Escherichia coli, Klebsiella pneumoniae, Klebsiella oxytoca, Morganella morganii, Haemophilus influenzae* (including beta-lactamase-producing strains) and *Haemophilus parainfluenzae* (including beta-lactamase-producing strains). The multidrug-resistant *Streptococcus pneumoniae* isolates are strains resistant to two or more of the following antibiotics: penicillin (minimum inhibitory concentration (MIC)>2 mcg/ml), second generation cephalosporins (e.g., cefuroxime), macrolides, chloramphenicol, fluoroquinolones, tetracyclines and trimethoprim/sulfamethoxazole.

In some embodiments, the methods include treating bacterial infections due to facultative Gram-positive microorganisms, e.g., Group CFG streptococci, Viridans group streptococci and *Streptococcus pneumoniae* (penicillin-intermediate, penicillin-resistant or multidrug-resistant); facultative Gram-negative microorganisms, e.g., *Citrobacter koseri* (ceftazidime-susceptible), *Citrobacter freundii* (ceftazidime-susceptible), *Enterobacter cloacae* (ceftazidime-susceptible), *Enterobacter aerogenes* (ceftazidime-susceptible), *Haemophilus influenzae* (beta-lactamase-negative, ampicillin-resistant), *Moraxella catarrhalis, Neisseria gonorrhoeae, Neisseria meningitidis, Pasturella multocida, Providencia rettgeri* (ceftazidime-susceptible), *Proteus mirabilis* (ceftazidime-susceptible), *Salmonella* spp. (ceftazidime-susceptible) and *Shigella* spp (ceftazidime-susceptible); and anaerobic microorganisms, e.g., *Clostridium* spp., *Finegoldia magna, Propionibacterium acnes, Fusobacterium nucleatum* and *Fusobacterium necrophorum*.

In exemplary embodiments, ceftaroline or a prodrug thereof may be administered to patients in need thereof for the treatment of complicated skin and skin structure infections (cSSSI). The cSSSI may be due to Gram-positive and Gram-negative microorganisms, such as *Staphylococcus, Streptococcus, Enterococcus, Escherichia, Klebsiella* and *Morganella*. In exemplary embodiments, the microorganism may be a *Staphylococcus aureus* including methicillin-susceptible and methicillin-resistant isolates. In other embodiments, the cSSSI may be due to *Streptococcus pyogenes, Streptococcus agalactiae, Streptococcus dysgalactiae* or *Streptococcus anginosus* group (including *S. anginosus, S. intermedius*, and *S. constellatus*). In still other embodiments, the cSSSI may be due to *Enterococcus faecalis*, e.g., an ampicillin-susceptible isolate of *Enterococcus faecalis*.

In some embodiments, the cSSSI may be due to *Escherichia coli*, *Klebsiella pneumoniae*, *Klebsiella oxytoca* or *Morganella morganii*.

In some embodiments, ceftaroline or a prodrug thereof may be administered to patients in need thereof for the treatment of community-acquired bacterial pneumonia (CABP). The CABP may be due to Gram-positive and Gram-negative microorganisms, such as *Streptococcus*, *Staphylococcus*, *Haemophilus*, *Haemophilis*, *Klebsiella* and *Escherichia*. In exemplary embodiments, the infection may be due to susceptible isolates of *Streptococcus pneumoniae*, *Staphylococcus aureus*, *Haemophilus influenzae*, *Haemophilus parainfluenzae*, *Klebsiella pneumoniae* or *Escherichia coli*. In exemplary embodiments, the microorganism may be *Streptococcus pneumoniae*. The strain of *Streptococcus pneumoniae* may be penicillin-susceptible, penicillin-resistant or multidrug resistant. In further embodiments, the microorganism may be *Streptococcus pneumoniae* serotype 19A. In some embodiments, the CABP may be associated with concurrent bacteremia. In other exemplary embodiments, the microorganism may be *Staphylococcus aureus*. The strain or isolate of *Staphylococcus aureus* may be methicillin-susceptible or methicillin-resistant. In still other exemplary embodiments, the microorganism may be *Haemophilus influenzae*, *Klebsiella pneumoniae* or *Escherichia coli*. In exemplary embodiments, the microorganism may be a β-lactamase-nonproducing ampicillin-resistant (BLNAR) strain of *Haemophilus influenzae*. In other embodiments, the CABP may be due to *Enterobacter*, *Proteus*, *Serratia* or *Moraxella*. In further embodiments, the CABP may be due to *Enterobacter aerogenes*, *Proteus mirabilis*, *Serratia marcescens* or *Moraxella catarrhalis*.

In exemplary embodiments, the methods include treatment of cSSSI or CABP by administering to a patient in need thereof, a therapeutically effective amount of ceftaroline or a prodrug thereof (e.g., ceftaroline fosamil). In some embodiments, the methods include administering ceftaroline or a pharmaceutically acceptable salt or a solvate thereof. In other embodiments, the methods include administering ceftaroline prodrug or a pharmaceutically acceptable salt or a solvate thereof. In exemplary embodiments, the prodrug may be a phosphono prodrug. In some examples, the ceftaroline prodrug may be ceftaroline fosamil. In some embodiments, the ceftaroline fosamil may be a hydrous from, e.g., a monohydrate form. In still other embodiments, ceftaroline fosamil may be in an anhydrous form. In some embodiments, ceftaroline or a prodrug thereof may be a solvate form. For example, ceftaroline or prodrug of ceftaroline may be an acetic acid solvate form, such as, ceftaroline fosamil monohydrate, acetic acid solvate.

In some embodiments, methods of treating cSSSI or CABP by administering to a patient in need thereof, a therapeutically effective amount of (6R,7R)-7-{(2Z)-2-(ethoxyimino)-2-[5-(phosphonoamino)-1,2,4-thiadiazol-3-yl]acetamido}-3-{[4-(1-methylpyridin-1-ium-4-yl)-1,3-thiazol-2-yl]sulfanyl}-8-oxo-5-thia-1-azabicyclo[4.2.0]oct-2-ene-2-carboxylate (i.e., ceftaroline fosamil) are provided.

In some embodiments, the methods for treating bacterial infection include administering between about 100 mg and about 2400 mg of ceftaroline or a prodrug thereof (e.g., ceftaroline fosamil). In further embodiments, ceftaroline or a prodrug thereof may be administered in an amount between about 100 mg and about 1200 mg. In some embodiments, ceftaroline or a prodrug thereof may be administered in an amount between about 200 mg and about 1000 mg. In exemplary embodiments, the amount may be about 100 mg, about 200 mg, about 300 mg, about 400 mg, about 500 mg, about 600 mg, about 700 mg, about 800 mg, about 900 mg, about 1000 mg, about 1100 mg or about 1200 mg. In certain embodiments, the amount may be about 400 mg. In other embodiments, the amount may be about 600 mg. In still other embodiments, the amount may be about 800 mg. In certain embodiments, the amount may be about 1200 mg. The methods include administering a dosage form comprising ceftaroline or a prodrug thereof (e.g., ceftaroline fosamil) in an amount as described above. For example, the dosage forms may comprise between about 200 mg and about 800 mg of ceftaroline or a prodrug thereof (e.g., ceftaroline fosamil).

The amount may be administered in a single dose or multiple divided doses per day. For example, the amount may be administered as a single daily dose. In exemplary embodiments, about 800 mg of ceftaroline of a prodrug thereof (e.g., ceftaroline fosamil) may be administered per day. In other exemplary embodiments, about 1200 mg of ceftaroline of a prodrug thereof (e.g., ceftaroline fosamil) may be administered per day. In some embodiments, the amount may be administered in two to eight doses per day. For example, about 400 mg of ceftaroline of a prodrug thereof (e.g., ceftaroline fosamil) may be administered every 12 hours (i.e. twice a day). In some examples, about 600 mg of ceftaroline of a prodrug thereof (e.g., ceftaroline fosamil) may be administered every 12 hours (i.e. twice a day).

In some embodiments, ceftaroline or a prodrug thereof may be administered parenterally. Suitable methods for parenteral administration include, but are not limited to, administering a sterile aqueous preparation of the compound, which preferably is isotonic with the blood of the recipient (e.g., physiological saline solution). Such preparations may include suspending agents and thickening agents and liposomes or other microparticulate systems, which are designed to target the compound to blood components or one or more organs. The preparation may be presented in a unit-dose or multi-dose form.

Parenteral administration may be intravenous, intra-arterial, intrathecal, intramuscular, subcutaneous, intramuscular, intra-abdominal (e.g., intraperitoneal), etc. In some embodiments, the parenteral administration may be effected by infusion pumps (external or implantable) or any other suitable means appropriate to the desired administration modality.

Ceftaroline or a prodrug thereof (e.g., ceftaroline fosamil) may be administered as a solution or suspension in a solvent, such as water, physiological saline, about a 5% to about 10% sugar (e.g., glucose, dextrose) solution, or combinations thereof. In exemplary embodiments, ceftaroline or a prodrug thereof may be administered intravenously, such as, by infusion. In some embodiments, ceftaroline or a prodrug thereof may be administered by intravenous infusion over one hour. In other embodiments, ceftaroline or a prodrug thereof may be administered through continuous or prolonged intravenous infusion. In still other embodiments, ceftaroline or a prodrug thereof may be administered intramuscularly. For intramuscular administration of higher doses, the injection may occur at two or more intramuscular sites.

In some embodiments, the methods may include administering ceftaroline or a prodrug thereof every 4 hours, 6 hours, 8 hours, 12 hours, 18 hours or every 24 hours. For example, ceftaroline or a prodrug thereof may be administered every 12 hours intravenously by infusion over one hour. In other embodiments, the methods may include administering ceftaroline or a prodrug thereof through continuous or prolonged infusion. For example, ceftaroline or a prodrug thereof may be administered by infusion over 2 hours, 3 hours, 4 hours, 5 hours, 6 hours, 7 hours, 8 hours, 9 hours, 10 hours, 11 hours or 12 hours. In other embodiments, the duration of infusion may be more than 12 hours, e.g., 13 hours, 14 hours, 15 hours, 16 hours, 17 hours, 18 hours, 19 hours, 20 hours, 21 hours or 22 hours, 23 hours or 24 hours. For example, about 400 mg of ceftaroline or a prodrug thereof may be administered by infusion over 12 hours. In another example, about 600 mg of ceftaroline or a prodrug thereof may be administered by infusion over 12 hours.

The duration of treatment may depend on the severity and site of infection and the patient's clinical and bacteriological progress. In some embodiments, the treatment may last between about 5 to 14 days. In other embodiments, the treatment may last between about 5 to 7 days. For example, about 400 mg of ceftaroline or a prodrug thereof may be administered every 24 hours for about five to fourteen days. In further embodiments, about 400 mg of ceftaroline or a prodrug thereof may be administered every 24 hours for about five to ten days. In other embodiments, about 400 mg of ceftaroline or a prodrug thereof may be administered every 24 hours for about five to seven days.

In other embodiments, about 400 mg of ceftaroline or a prodrug thereof may be administered every 12 hours for about five to fourteen days. In other embodiments, about 400 mg of ceftaroline or a prodrug thereof may be administered every 12 hours for about five to ten days. In still other embodiments, about 400 mg of ceftaroline or a prodrug thereof may be administered every 12 hours for about five to seven days.

In other embodiments, about 400 mg of ceftaroline or a prodrug thereof may be administered every 8 hours for about five to fourteen days. For example, about 400 mg of ceftaroline or a prodrug thereof may be administered every 8 hours for about five to ten days. In further embodiments, about 400 mg of ceftaroline or a prodrug thereof may be administered every 8 hours for about five to seven days.

In some embodiments, about 600 mg of ceftaroline or a prodrug thereof may be administered every 24 hours for about five to fourteen days. For example, about 600 mg of ceftaroline or a prodrug thereof may be administered every 24 hours for about five to ten days. In exemplary embodiments, about 600 mg of ceftaroline or a prodrug thereof may be administered every 24 hours for about five to seven days.

In exemplary embodiments, about 600 mg of ceftaroline or a prodrug thereof may be administered every 12 hours for about five to fourteen days. In other embodiments, about 600 mg of ceftaroline or a prodrug thereof may be administered every 12 hours for about five to ten days. In still other embodiments, about 600 mg of ceftaroline or a prodrug thereof may be administered every 12 hours for about five to seven days.

In certain embodiments, about 600 mg of ceftaroline or a prodrug thereof may be administered every 8 hours for about five to fourteen days. In some embodiments, about 600 mg of ceftaroline or a prodrug thereof may be administered every 8 hours for about five to ten days. In other embodiments, about 600 mg of ceftaroline or a prodrug thereof may be administered every 8 hours for about five to seven days.

In exemplary embodiments, the methods include treating complicated skin and skin structure infections (cSSSI) by administering to a patient in need thereof about 600 mg ceftaroline or a prodrug thereof (e.g., ceftaroline fosamil) every 12 hours intravenously through infusion over one hour for five to fourteen days.

In other exemplary embodiments, the methods include treating community-acquired bacterial pneumonia (CABP) by administering about 600 mg ceftaroline or a prodrug thereof (e.g., ceftaroline fosamil) every 12 hours intravenously through infusion over one hour for five to seven days.

In some embodiments, the methods of treatment may require dosage adjustment depending on the patient to be treated. For example, patients with a creatinine clearance of more than 50 ml/min may not require dosage adjustment. Such patients may be treated by administering about 600 mg of ceftaroline or a prodrug thereof (e.g., ceftaroline fosamil) intravenously every 12 hours, such as, for example, by infusion over one hour. In patients with impaired renal function with creatinine clearance of less than 50 ml/min, adjustment of the dosage regimen may be needed to avoid the accumulation of ceftaroline due to decreased clearance. For example, patients with creatinine clearance of about 10 ml/min to about 50 ml/min may be treated by administering about 400 mg ceftaroline or a prodrug thereof (e.g., ceftaroline fosamil) intravenously every 12 hours, such as, for example, by infusion over one hour.

Creatinine clearance can be estimated using the Cockcroft-Gault formula. For example, creatinine clearance may be calculated using the following formula, which represents a steady state of renal function.

Creatinine clearance (ml/min)=Weight (kg)×(140−age in years)/72×serum creatinine (mg/dl)   Males:

Creatinine clearance (ml/min)=0.85×value calculated for males   Females:

In some embodiments, a supplementary dose of ceftaroline or a prodrug thereof may be recommended if ceftaroline or a prodrug thereof is administered prior to hemodialysis. The amount of supplementary dose to be administered may depend on number of hours between administration of ceftaroline or a prodrug thereof and hemodialysis.

In some embodiments, the methods comprise providing a dosage form comprising about 200 mg to about 800 mg of ceftaroline or a prodrug thereof and adding about 20 ml of sterile water to the dosage form to form a constituted solution that has a pH of between about 4 and about 7, and administering the constituted solution over a period of about one hour. In some examples, the constituted solution has a pH of about 4.8 to about 6.5. In other examples, the constituted solution has a pH of about 4.5 to about 6.5.

In other embodiments, the methods comprise providing a dosage form comprising about 400 mg of ceftaroline or a prodrug thereof and administering a constituted solution comprising the dosage form over a period of about one hour to patients with a creatinine clearance from about 10 to about 50 ml/min. In further embodiments, the administration is repeated every 12 hours over a period of about five to fourteen days. In some examples, the administration is repeated every 12 hours over a period of about five to seven days.

In still other embodiments, the methods comprise providing a dosage form comprising about 600 mg of ceftaroline or a prodrug thereof and administering a constituted solution comprising the dosage form over a period of about one hour. In further embodiments, the administration is repeated every 12 hours over a period of about five to fourteen days. In some examples, the administration is repeated every 12 hours over a period of about five to seven days.

In some examples, the methods comprise providing a dosage form comprising about 600 mg of ceftaroline or a prodrug thereof and administering a constituted solution comprising the dosage form over a period of about one hour such that the dosage forms provide an in vivo plasma profile for ceftaroline comprising a Cmax of about 15 to about 30 μg/ml and an AUC of about 45 to about 75 μg h/ml.

In some embodiments, the methods comprise providing dosage forms comprising about 100 mg to about 1200 mg of ceftaroline or a prodrug thereof that provide an in vivo plasma profile for ceftaroline comprising a mean Tmax of more than about 10 min. For example, the plasma profile comprises a mean Tmax of more than about 15 minutes, 30 minutes, 45 minutes, 1 hour, 1.5 hours or about 2 hours. In exemplary embodiments, the plasma profile comprises a mean Tmax of about 30 minutes to about 4 hours, such as about 1.6 hours, about 2 hours, about 2.5 hours or about 3 hours.

In some embodiments, the methods comprise administering to the patient a dosage form comprising about 200 mg to about 800 mg ceftaroline or prodrug thereof and informing the patient that the dosage form is contraindicated in patients with known serious hypersensitivity or in patients who have demonstrated anaphylactic reactions to beta-lactams.

In some embodiments, the methods include providing a dosage form comprising ceftaroline or a prodrug thereof (e.g., ceftaroline fosamil) and providing instructions on administration of the dosage form.

In some embodiments, the methods include providing a dosage form comprising about 200 mg to about 1200 mg ceftaroline or a prodrug thereof (e.g., ceftaroline fosamil) and providing instructions to prepare a solution comprising the dosage form for intravenous or intramuscular administration. In exemplary embodiments, the methods comprise providing the dosage form as a sterile dry powder in a vial and providing instructions to constitute the vial with a diluent for intravenous administration. For example, the instructions may include constituting the vial with a specified amount of diluent, gently shaking until the powder is completely dissolved, withdrawing a specified volume of the constituted solution and adding it to an infusion bag containing up to about 250 ml of infusion solution and gently shaking to ensure complete mixing of the drug product. The infusion solutions include, but are not limited to, 0.9% sodium chloride (normal saline), 5% dextrose, 2.5% dextrose and 0.45% sodium chloride and lactated Ringer's solution. In exemplary embodiments, the instructions may further warn that the constituted solution is not for direct injection.

In exemplary embodiments, about 400 mg of ceftaroline or a prodrug thereof (e.g., ceftaroline fosamil) may be reconstituted with about 20 ml of diluent and administered by infusion over about 1 hour. In other embodiments, about 600 mg of ceftaroline or a prodrug thereof (e.g., ceftaroline fosamil) may be reconstituted with about 20 ml of diluent and administered by infusion over about 1 hour. In some embodiments, the reconstituted solution may be held for about one hour prior to transfer and dilution in the infusion bag. In other embodiments, ceftaroline or a prodrug thereof is reconstituted in sterile water for injection and administered immediately. In particular embodiments, ceftaroline or a prodrug thereof may be reconstituted using I.V. bags containing normal saline. The I.V. bags can be stored at room temperature for up to about 6 hours or at 2-8° C. for up to about 24 hours prior to administration. In some embodiments, it may not be advisable to freeze the constituted solution.

In other embodiments, the dosage form is provided in a frozen bag or a pre-filled frozen syringe. In exemplary embodiments, the frozen bags may comprise about 1 mg/ml to 20 mg/ml ceftaroline or prodrug thereof (e.g., ceftaroline fosamil). In some examples, the frozen bag may comprise about 2 mg/ml, about 3 mg/ml, about 4 mg/ml, about 5 mg/ml, about 6 mg/ml, about 7 mg/ml, about 8 mg/ml, about 9 mg/ml, about 10 mg/ml, about 11 mg/ml or about 12 mg/ml of ceftaroline or prodrug thereof (e.g., ceftaroline fosamil). In addition, the frozen bags may comprise about 0.5 mg/ml to about 20 mg/ml of L-arginine. In exemplary embodiments, the frozen bags may comprise about 0.5 mg/ml, about 1 mg/ml, about 2 mg/ml, about 3 mg/ml, about 4 mg/ml, about 5 mg/ml, about 6 mg/ml, about 7 mg/ml, about 8 mg/ml, about 9 mg/ml or about 10 mg/ml of L-arginine. In some embodiments, the frozen bags may have a pH ranging from about 4.5 to about 7. In exemplary embodiments, the pH may be between about 5.5 and about 7.

In exemplary embodiments, the present invention provides frozen bags comprising compositions comprising ceftaroline or a prodrug thereof (e.g., ceftaroline fosamil) that are surprisingly and unexpectedly stable. For example, the compositions may include formulations comprising ceftaroline or a prodrug thereof (e.g., ceftaroline fosamil) and 0.9% sodium chloride, 5% dextrose, 2.5% dextrose, 0.45% sodium chloride or lactated Ringer's solution.

In some embodiments, the compositions comprising ceftaroline or a prodrug thereof (e.g., ceftaroline fosamil) may include 0.9% sodium chloride and be surprisingly and unexpectedly stable as demonstrated by the level of one or more impurities or adducts. For example, the total impurities may not be more than about 5%. In other embodiments, the compositions may comprise not more than about 5% U3, not more than about 0.6% U1 and/or not more than about 0.6% U6. In exemplary embodiments, the total impurities in frozen bags may be less than 5%. In some examples, the frozen bags may comprise about 0.05% to about 5% total impurities. In specific embodiments, the frozen bags may comprise about 0.05% to about 5% U3, about 0.05% to about 0.6% U1 or about 0.05% to about 0.6% U6. For example, the compositions may comprise about 0.05% to about 5% U3 after storage at −20° C. after 0 to 6 months. In other embodiments, the compositions may comprise about 0.05% to about 0.6% U1 after storage at −20° C. after 0 to 6 months. In still other embodiments, the compositions may comprise about 0.05% to about 0.6% U6 after storage at −20° C. after 0 to 6 months.

In further embodiments, instructions on administration of the dosage form are provided. For example, a subject is instructed to thaw the frozen bag or the frozen syringe prior to administration. The subject may be further instructed to dilute the composition with a compatible diluent prior to administration.

In some embodiments, the method comprises preparing a solution of ceftaroline or a prodrug thereof for intramuscular administration. In exemplary embodiments, ceftaroline or a prodrug thereof is reconstituted with a specified amount of diluent and gently shaken until the powder is completely dissolved. In specific embodiments, the reconstituted solution is administered by deep intramuscular injection into a large muscle mass, such as, the gluteal muscles or lateral part of the thigh. In exemplary embodiments, the reconstituted intramuscular solution is to be used within one about hour of preparation. For example, about 400 mg of ceftaroline or a prodrug thereof may be reconstituted using about 2 ml of diluent and used for intramuscular administration. In other exemplary embodiments, about 600 mg of ceftaroline or a prodrug thereof may be reconstituted using about 2 ml of diluent and used for intramuscular administration.

In exemplary embodiments, the methods include providing information that constituted solution containing ceftaroline or a prodrug thereof should be visually inspected for particulate matter and/or discoloration prior to administration. Further information that the constituted solutions may be yellow in color or infusion solutions may be clear or light to dark yellow in color may be provided. The color may depend on concentration and diluents used. The color of compositions comprising ceftaroline or a prodrug thereof may darken depending on storage conditions. In such embodiments, the product potency may not be adversely affected. The diluents that could be used for intravenous administration include, but are not limited to, 0.9% Sodium Chloride Injection, USP (normal saline); 5% Dextrose Injection, USP; 2.5% Dextrose and 0.45% Sodium Chloride Injection, USP and Lactated Ringer's Injection, USP.

In further embodiments, the methods may provide instructions not to mix ceftaroline or a prodrug thereof with solutions containing other drugs.

In some embodiments, information that ceftaroline or prodrug thereof is contraindicated in patients with known serious hypersensitivity or in patients who have demonstrated anaphylactic reactions to beta-lactams may be provided. In further embodiments, the patient may be informed that serious and occasionally fatal hypersensitivity (anaphylactic) reactions and serious skin reactions have been reported in patients receiving beta-lactam antibiotics and that such reactions are more likely to occur in individuals with a history of sensitivity to multiple allergens. In some embodiments, a careful inquiry may be needed to determine whether the subject to be treated has had a previous hypersensitivity reaction to other carbapenems, cephalosporins, penicillins or other allergens before treatment is initiated. In some embodiments, the patient is instructed to discontinue the drug if an allergic reaction occurs.

In some embodiments, information on adverse events may be provided. For example, the information that most common adverse reactions occurring in about 4% or more patients are diarrhea, nausea and headache may be provided.

In some embodiments, methods for treating bacterial infection, e.g., cSSSI and CABP include providing a pharmaceutical product comprising a dosage form comprising ceftaroline or a prodrug thereof (e.g., ceftaroline fosamil) and published material. For example, the pharmaceutical product may be a vial, a bag or a syringe, with or without a packaging material. In exemplary embodiments, the product may be a vial comprising about 400 mg or about 600 mg of sterile powder comprising ceftaroline or a prodrug thereof (e.g., ceftaroline fosamil). The vial may comprise any of the compositions described above. The published material may contain information on administration of the dosage form. The published material may be a product insert, flyer, brochure, or a packaging material for the dosage form such as a bag, or the like. In exemplary embodiments, the published material contains instructions to constitute a vial containing the dosage form with a specified amount of diluent (e.g., 20 ml for intravenous and 2 ml for intramuscular administration) and gently shake until the powder is completely dissolved. In further embodiments, the material contains instructions to withdraw a specified volume of the constituted solution and add it to an infusion bag containing a diluent, such as, 250 ml of 0.9% sodium chloride (normal saline), 5% dextrose, 2.5% dextrose and 0.45% sodium chloride or Lactated Ringer's solution and gently shake to ensure complete mixing of the drug product. The published material may further state that the constituted solution is not for direct injection. In exemplary embodiments, the material contains instructions that about 400 mg of ceftaroline or a prodrug thereof is to be reconstituted with about 20 ml of diluent and administered by infusion over about 1 hour. In other exemplary embodiments, the material contains instructions that about 600 mg of ceftaroline or a prodrug thereof is to be reconstituted with about 20 ml of diluent and administered by infusion over about 1 hour. In some examples, the material contains instructions that that about 400 mg of ceftaroline or a prodrug thereof may be reconstituted using about 2 ml of diluent and used for intramuscular administration. In other exemplary embodiments, the material contains instructions that about 600 mg of ceftaroline or a prodrug thereof may be reconstituted using about 2 ml of diluent and used for intramuscular administration.

For products, such as frozen bags and pre-filled syringes, the material may include instructions to thaw the frozen bag or the frozen syringe prior to administration. In further embodiments, the material may have instructions to dilute the composition with a compatible diluent prior to administration.

In some embodiments, the methods comprise providing a dosage form comprising about 100 mg to about 1200 mg ceftaroline or a prodrug thereof to a patient in need thereof and informing the patient that the dosage form is contraindicated in patients with known serious hypersensitivity or in patients who have demonstrated anaphylactic reactions to beta-lactams.

In further embodiments, the patient may be informed that serious and occasionally fatal hypersensitivity (anaphylactic) reactions and serious skin reactions have been reported in patients receiving beta-lactam antibiotics and that such reactions are more likely to occur in individuals with a history of sensitivity to multiple allergens. In some embodiments, a careful inquiry may be needed to determine whether the subject to be treated has had a previous hypersensitivity reaction to other carbapenems, cephalosporins, penicillins or other allergens before treatment is initiated. In some embodiments, the patient is instructed to discontinue the drug if an allergic reaction occurs.

In some embodiments, the methods comprise providing a dosage form comprising about 100 mg to about 1200 mg of ceftaroline or a prodrug thereof and providing information on interaction of the ceftaroline or prodrug thereof with other antimicrobial agents. For example, the methods may comprise informing that there is no antagonism between ceftaroline or a prodrug thereof and other commonly used antibacterial agents. Examples of such antibacterial agents, include but are not limited to, vancomycin, linezolid, daptomycin, levofloxacin, azithromycin, amikacin, aztreonam, tigecycline, and meropenem. In some embodiments, the methods may comprise providing information that there is synergy between ceftaroline and other antimicrobial agents. For example, information that there is demonstrated synergy between ceftaroline or a prodrug thereof and an antibacterial or antimicrobial agent, e.g., amikacin may be provided. Examples of other antibacterial agents, include but are not limited to, vancomycin, linezolid, daptomycin, levofloxacin, azithromycin, aztreonam, tigecycline, and meropenem.

Unless defined otherwise, all technical and scientific terms used herein generally have the same meaning as commonly understood by one of ordinary skill in the art to which this invention belongs.

The term "prodrug" means a compound that is a drug precursor, which upon administration to a subject undergoes chemical conversion by metabolic or chemical processes to yield a compound, which is an active moiety. Suitable prodrugs of ceftaroline include, but are not limited to phosphonocepehem derivatives, such as, e.g., 7β-[2(Z)-ethoxyimino-2-(5-phosphonoamino-1,2,4-thiadiazol-3-yl)acetamido]-3-[4-(1-methyl-4-pyridinio)-2-thiazolythio]-3-cephem-4-carboxylate.

Solvates of a compound may form when a solvent molecule(s) is incorporated into the crystalline lattice structure of ceftaroline or a prodrug thereof molecule during, for example, a crystallization process. Suitable solvates include, e.g., hydrates (monohydrate, sesquihydrate, dihydrate), solvates with organic compounds (e.g., $CH_3CO_2H$, $CH_3CH_2CO_2H$, $CH_3CN$), and combinations thereof.

The term "consisting essentially of" as used herein for compositions or dosage forms means that ceftaroline or a prodrug thereof (e.g, ceftaroline fosamil) is the only active ingredient in the compositions or dosage forms. An "active ingredient" as used herein refers to an antimicrobial agent or an antibacterial agent or an agent which is effective for the treatment of a bacterial infection.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per practice in the art. Alternatively, "about" with respect to the compositions can mean plus or minus a range of up to 20%, preferably up to 10%, more preferably up to 5%. Alternatively, particularly with respect to biological systems or processes, the term can mean within an order of magnitude, preferably within 5-fold, and more preferably within 2-fold, of a value. Where particular values are described in the application and claims, unless otherwise stated the term "about" means within an acceptable error range for the particular value. For example, when referring to a period of time, e.g., hours, the present values (±20%) are more applicable. Thus, 6 hours can be, e.g., 4.8 hours, 5.5 hours, 6.5 hours, 7.2 hours, as well as the usual 6 hours.

The terms "treat," "treatment," and "treating" refer to one or more of the following: relieving or alleviating at least one symptom of a bacterial infection in a subject; relieving or alleviating the intensity and/or duration of a manifestation of bacterial infection experienced by a subject; and arresting, delaying the onset (i.e., the period prior to clinical manifestation of infection) and/or reducing the risk of developing or worsening a bacterial infection.

The term "community acquired pneumonia" as used herein is equivalent and has been used interchangeably with the term "community acquired bacterial pneumonia."

The term "therapeutically effective" applied to dose or amount refers to that quantity of a compound or pharmaceutical composition that is sufficient to result in a desired activity upon administration to a mammal in need thereof. An "effective amount" means the amount of a compound according to the invention that, when administered to a patient for treating an infection or disease is sufficient to effect such treatment. The "effective amount" will vary depending on the active ingredient, the state of infection, disease or condition to be treated and its severity, and the age, weight, physical condition and responsiveness of the mammal to be treated.

EXAMPLES

The following examples are merely illustrative of the present invention and should not be construed as limiting the scope of the invention in any way as many variations and equivalents that are encompassed by the present invention will become apparent to those skilled in the art upon reading the present disclosure.

Example 1

The prodrug, ceftaroline fosamil, is rapidly converted into bioactive ceftaroline in plasma. The mean pharmacokinetic parameters of ceftaroline in adults with normal renal function after single and multiple 60-minute IV infusions of 600 mg ceftaroline fosamil administered every 12 hours are summarized in Table 1. The standard deviation is shown in brackets. Pharmacokinetic characteristics were similar for single and multiple dose administration.

TABLE 1

Mean Pharmacokinetic Parameters of Ceftaroline IV in Adults

| Parameter | Single 600 mg Dose Administered as a 60 Minute Infusion | Multiple 600 mg Doses Administered Every 12 Hours as 60 Minute Infusions |
|---|---|---|
| $C_{max}$ (μg/mL) | 19.0 (0.71) | 21.3 (4.10) |
| AUC (μg · h/mL) * | 56.8 (8.94) | 56.2 (8.90) |
| $t_{1/2}$ (h) | 1.60 (0.38) | 2.66 (0.40) |
| CL/Fm (L/h) | 9.58 (1.85) | 9.60 (1.40) |

* $AUC_{0-\infty}$ for single-dose administration, $AUC_{0-tau}$ for multiple-dose administration The $C_{max}$ and AUC of ceftaroline increased approximately in proportion to increases in dose within the dose range of 50 to 1000 mg. No appreciable accumulation of ceftaroline fosamil or ceftaroline was observed following multiple IV infusions of 600 mg administered every 8 or 12 hours for up to 14 days in subjects with normal renal function. The binding of ceftaroline to human plasma protein was low (approximately 20%) and decreased only slightly with increasing concentrations.

The prodrug, ceftaroline fosamil, was rapidly converted into bioactive ceftaroline in plasma, and the conversion appeared to be mediated by a phosphatase enzyme. Hydrolysis of the beta-lactam ring of ceftaroline subsequently occurred to form the microbiologically inactive, open-ring metabolite ceftaroline M-1. The mean plasma ceftaroline M-1 to ceftaroline AUC ratio following a single 600 mg IV infusion of ceftaroline fosamil in healthy subjects was approximately 20-30%. In pooled human liver microsomes, low (<12%) metabolic turnover was observed for ceftaroline fosamil and ceftaroline. These studies indicate that hepatic CYP450 enzymes are unlikely to significantly metabolize ceftaroline fosamil or ceftaroline.

Ceftaroline and its metabolites are primarily eliminated by the kidneys. The mean plasma terminal elimination half-life of ceftaroline in healthy adults with normal renal function was approximately 2.5 hours.

Following administration of a single 600 mg IV dose of radiolabeled ceftaroline fosamil to healthy male adults, approximately 87% of radioactivity was recovered in urine and 6% in feces. The majority of the radioactivity (~90%) was recovered within 48 hours. Of the radioactivity recovered in urine, approximately 64% was excreted as ceftaroline and approximately 2% as ceftaroline-M-1.

Special Populations

Following administration of a single 600 mg intravenous dose of ceftaroline fosamil, the mean AUC of ceftaroline in subjects with mild (50 mL/min<CrCl≤80 mL/min) or moderate (30 mL/min<CrCl≤50 mL/min) renal impairment was increased by 19% and 52%, respectively, compared to mean values in healthy subjects with normal renal function (CrCl>80 mL/min). Following administration of a single 400 mg intravenous dose of ceftaroline fosamil, the mean AUC of ceftaroline in subjects with severe (CrCl≤30 mL/min) renal impairment was increased by 115% compared to mean values in healthy subjects with normal renal function.

A single 400 mg dose of ceftaroline fosamil was administered to subjects with end stage renal disease (ESRD) either 4 hours prior to or 1 hour after hemodialysis (HD). The mean ceftaroline AUC following the pre- and post-HD infusion was increased by approximately 89% and 167%, respectively, compared to mean values in healthy subjects with normal renal function. The mean recovery of ceftaroline in the dialysate following a 4-hour HD session was 76.5 mg, or 21.6% of the administered dose.

Following administration of a 600 mg intravenous dose of ceftaroline fosamil to healthy elderly subjects (≥65 years of age), the mean AUC of ceftaroline was slightly higher (~33%) than that in healthy young adult subjects (18-45 years of age). $C_{max}$ was not significantly different between the elderly and younger subjects. The difference in AUC was attributable to decreased renal function in the elderly subjects and was not believed to be clinically significant.

The pharmacokinetics of ceftaroline were evaluated in adolescent patients (ages 12 to 17) with normal renal function. The mean values of $C_{max}$ and AUC for ceftaroline observed in adolescent subjects who received 8 mg/kg ceftaroline fosamil (or 600 mg for subjects weighing >75 kg) were about 10% and 23% less than the values observed in adult subjects following administration of a 600 mg dose of ceftaroline fosamil.

Gender

In Phase 1 studies in healthy subjects, $C_{max}$ and AUC for ceftaroline were similar between males and females, although there was a trend for slightly higher AUC (6-15%) and $C_{max}$ (17-22%) in female subjects. Population pharmacokinetic analysis of data from Phase 1, 2 and 3 clinical studies did not identify clinically meaningful increases in ceftaroline exposure based on gender. No dose adjustment is required based on gender.

Drug Interactions

In vitro studies in human liver microsomes suggest that neither ceftaroline fosamil nor ceftaroline inhibits the major cytochrome P450 isoenzymes CYP1A1, CYP1A2, CYP2A6, CYP2B6, CYP2C8, CYP2C9, CYP2C19, CYP2D6, CYP2E1 and CYP3A4. In vitro studies in human hepatocytes have also demonstrated that ceftaroline fosamil, ceftaroline, and its inactive open-ring metabolite are not inducers of CYP1A2, CYP2B6, CYP2C8, CYP2C9, CYP2C19, or CYP3A4/5. Therefore, ceftaroline fosamil is not expected to inhibit or induce the clearance of drugs that are metabolized by these metabolic pathways in a clinically relevant manner.

Exploratory population PK analysis did not identify any clinically relevant increases in ceftaroline exposure ($C_{max}$ and AUC) in patients with cSSSI or CABP who were taking concomitant medications that are known inhibitors, inducers, and substrates of the cytochrome P450 system. Thus, the present example establishes that ceftaroline and prodrugs thereof (e.g., ceftaroline fosamil) are surprisingly and unexpectedly safe and effective for the treatment of bacterial infections including community acquired pneumonia and cSSSI.

Example 2

A total of 1396 adults with clinically documented complicated skin and skin structure infections (cSSSI) were enrolled in two randomized, multi-center, multinational, double-blind, studies comparing 600 mg ceftaroline fosamil administered intravenously over 1 hour every 12 hours to vancomycin plus aztreonam [1 g vancomycin administered intravenously over 1 hour followed by 1 g aztreonam administered intravenously over 1 hour every 12 hours]. Patients with cSSSI (deep/extensive cellulitis, a major abscess, a wound infection [surgical or traumatic], infected insect bites, burns or ulcers, lower extremity infection in patients with diabetes mellitus or peripheral vascular disease), were enrolled in the studies. Treatment duration was 5 to 14 days. A switch to oral therapy was not allowed. The Modified Intent-to-Treat (MITT) population included all patients who received any amount of study drug according to their randomized treatment group. The Clinically Evaluable (CE) population included patients in the MITT population who demonstrated sufficient adherence to the protocol.

The primary efficacy endpoint was clinical response at the Test of Cure (TOC) visit in the co-primary CE and MITT populations (Table 2). Ceftaroline was non-inferior to vancomycin plus aztreonam. In a subgroup analysis (CE population), the comparative clinical cure rates between the ceftaroline group and the vancomycin plus aztreonam group were not affected by age, gender, race, ethnicity, or weight. Clinical cure rates at TOC by pathogen in the Microbiologically Evaluable (ME) population are presented in Table 3.

TABLE 2

Clinical Cure Rates at TOC from two Phase 3 Studies in cSSSI after 5 to 14 days of Therapy

|  | Ceftaroline fosamil n/N (%) | Vancomycin/ Aztreonam n/N (%) | Treatment Difference (2-sided 95% CI) |
| --- | --- | --- | --- |
| Integrated Studies |  |  |  |
| CE | 559/610 (91.6) | 549/592 (92.7) | −1.1 (−4.2, 2.0) |
| MITT | 595/693 (85.9) | 586/685 (85.5) | 0.3 (−3.4, 4.0) |
| cSSSI Study 1 |  |  |  |
| CE | 288/316 (91.1) | 280/300 (93.3) | −2.2 (−6.6, 2.1) |
| MITT | 304/351 (86.6) | 297/347 (85.6) | 1.0 (−4.2, 6.2) |
| cSSSI Study 2 |  |  |  |
| CE | 271/294 (92.2) | 269/292 (92.1) | 0.1 (−4.4., 4.5) |
| MITT | 291/342 (85.1) | 289/338 (85.5) | −0.4 (−5.8, 5.0) |

TABLE 3

Clinical Cure Rates by Infecting Pathogen from Microbiologically Evaluable Patients with cSSSI (Data from two integrated Phase 3 Studies)

|  | Ceftaroline fosamil n/N (%) | Vancomycin/ Aztreonam n/N (%) |
| --- | --- | --- |
| Gram-positive: |  |  |
| Staphylococcus aureus | 352/378 (93.1%) | 336/356 (94.4%) |
| MSSA (methicillin-susceptible) | 212/228 (93.0%) | 225/238 (94.5%) |
| MRSA (methicillin-resistant) | 142/152 (93.4%) | 115/122 (94.3%) |
| Streptococcus pyogenes | 56/56 (100%) | 56/58 (96.6%) |
| Streptococcus agalactiae | 21/22 (95.5%) | 18/18 (100%) |
| Streptococcus dysgalactiae | 13/13 (100%) | 15/16 (93.8%) |
| Streptococcus anginosus group[a] | 12/13 (92.3%) | 15/16 (93.8%) |
| Gram-negative: |  |  |
| Escherichia coli | 20/21 (95.2%) | 19/21 (90.5%) |
| Klebsiella pneumoniae | 17/18 (94.4%) | 13/14 (92.9%) |

TABLE 3-continued

Clinical Cure Rates by Infecting Pathogen from Microbiologically Evaluable Patients with cSSSI (Data from two integrated Phase 3 Studies)

| | Ceftaroline fosamil n/N (%) | Vancomycin/ Aztreonam n/N (%) |
|---|---|---|
| Klebsiella oxytoca | 10/12 (83.3%) | 6/6 (100%) |
| Morganella morganii | 11/12 (91.7%) | 5/6 (83.3%) |

[a]Includes S. anginosus, S. intermedius, and S. constellatus.

Example 3

A total of 1240 adults with a diagnosis of Community-Acquired Bacterial Pneumonia (CABP) were enrolled in two randomized, multi-center, multinational, double-blind, studies (Studies 1 and 2) comparing ceftaroline fosamil (600 mg administered intravenously over 1 hour every 12 h) to ceftriaxone (1 g ceftriaxone administered intravenously over 0.5 hour every 24 h). In both treatment groups of CABP Study 1, two doses of oral clarithromycin (500 mg q12h), were administered as adjunctive therapy starting on Study Day 1. No adjunctive macrolide therapy was used in CABP Study 2. Patients with new or progressive pulmonary infiltrate(s) on chest radiography and clinical signs and symptoms consistent with CABP with the need for hospitalization and IV therapy were enrolled in the studies. Treatment duration was 5 to 7 days. A switch to oral therapy was not allowed. The Modified Intent-to-Treat Efficacy (MITTE) population included all patients who received any amount of study drug according to their randomized treatment group and were in PORT (Pneumonia Outcomes Research Team) Risk Class III or IV. The Clinically Evaluable (CE) population included patients in the MITTE population who demonstrated sufficient adherence to the protocol.

The primary efficacy endpoint was the clinical response at the Test of Cure (TOC) visit in the co-primary CE and MITTE populations (Table 4). In a subgroup analysis (CE population), the comparative clinical cure rates between the ceftaroline group and the ceftriaxone group were not affected by age, gender, race, ethnicity, or weight. Clinical cure rates at TOC by pathogen in the Microbiologically Evaluable (ME) population are presented in Table 5.

TABLE 4

Clinical Cure Rates at TOC from Two Phase 3 Studies in CABP after 5 to 7 Days of Therapy

| | Ceftaroline fosamil n/N (%) | Ceftriaxone n/N (%) | Treatment Difference (2-sided 95% CI) |
|---|---|---|---|
| Integrated Studies | | | |
| CE | 387/459 (84.3%) | 349/449 (77.7%) | 6.7 (1.6, 11.8) |
| MITTE | 479/580 (82.6%) | 439/573 (76.6%) | 6.0 (1.4, 10.7) |
| CABP Study 1 | | | |
| CE | 194/224 (86.6%) | 183/234 (78.2%) | 8.4 (1.4, 15.4) |
| MITTE | 244/291 (83.8%) | 233/300 (77.7%) | 6.2 (−0.2, 12.6) |
| CABP Study 2 | | | |
| CE | 193/235 (82.1%) | 166/215 (77.2%) | 4.9 (−2.5, 12.5) |
| MITTE | 235/289 (81.3%) | 206/273 (75.5%) | 5.9 (−1.0, 12.7) |

TABLE 5

Clinical Cure Rates by Infecting Pathogen from Microbiologically Evaluable Patients with CABP (Data from Two Integrated Phase 3 clinical Studies)

| | Ceftaroline fosamil n/N (%) | Ceftriaxone n/N (%) |
|---|---|---|
| Gram-positive: | | |
| Streptococcus pneumoniae | 54/63 (85.7%) | 41/59 (69.5%) |
| MDRSP (multidrug-resistant [a]) | 4/4 (100%) | 1/4 (25.0%) |
| Staphylococcus aureus | 18/25 (72.0%) | 15/27 (55.6%) |
| MSSA (methicillin-susceptible) | 18/25 (72.0%) | 14/25 (56.0%) |
| Gram-negative: | | |
| Haemophilus influenzae | 15/18 (83.3%) | 17/20 (85.0%) |
| Haemophilus parainfluenzae | 16/16 (100%) | 15/17 (88.2%) |
| Escherichia coli | 10/12 (83.3%) | 9/12 (75.0%) |
| Klebsiella pneumoniae | 13/13 (100%) | 10/12 (83.3%) |

[a] MDRSP isolates are S. pneumoniae strains resistant to at least two or more of the following antibacterial classes: penicillins, macrolides, tetracyclines, fluoroquinolones, chloramphenicol, trimethoprim-sulfamethoxazole, and second-generation cephalosporins.

Example 4

A Phase 3, multicenter, randomized, double-blind, comparative study was conducted to evaluate the safety and efficacy of ceftaroline relative to ceftriaxone in the treatment of adult subjects with community-acquired pneumonia (CAP).

The primary objectives of the study was to determine the non-inferiority in the clinical cure rate for ceftaroline compared with that for ceftriaxone at test-of-cure (TOC) in the clinically evaluable (CE) and modified intent-to-treat efficacy (MITTE) populations in adult subjects with CAP. The secondary objectives of the study were to evaluate the following: clinical response at end-of-therapy (EOT); the microbiological favorable outcome rate at TOC; the overall (clinical and radiographic) success rate at TOC; the clinical and microbiological response by pathogen at TOC; clinical relapse at late follow-up (LFU); microbiological reinfection/recurrence at LFU; and safety.

317 subjects were randomized for ceftaroline and 310 subjects were randomized for ceftriaxone (intent-to-treat [ITT] Population). 315 subjects were in the ceftaroline and 307 subjects were in the ceftriaxone modified intent-to-treat (MITT) or safety population.

The following populations were analyzed for efficacy:

Modified intent-to-treat efficacy (MITTE) population: 289 (ceftaroline) and 273 (ceftriaxone);

Clinically evaluable (CE) population: 235 (ceftaroline) and 215 (ceftriaxone);

Microbiological modified intent-to-treat (mMITT) Population: 99 (ceftaroline) and 102 (ceftriaxone);

Microbiological modified intent-to-treat efficacy (mMITTE) Population: 90 (ceftaroline) and 88 (ceftriaxone); and Microbiologically evaluable (ME) Population: 85 (ceftaroline) and 76 (ceftriaxone).

The criteria for inclusion were:

1. Subjects were males and females 18 or more years of age.

2. Subjects had community-acquired pneumonia meeting the following criteria:

I. Radiographically confirmed pneumonia (new or progressive pulmonary infiltrate(s) on chest radiograph [CXR] or chest computed tomography [CT] scan consistent with bacterial pneumonia); and II. Acute illness (≤7 days' duration) with at least three of the following clinical signs or symptoms consistent with a lower respiratory tract infection: new or increased cough; purulent sputum or change in sputum character; auscultatory findings consistent with pneumonia (e.g., rales, egophony, findings of consolidation); dyspnea, tachypnea, or hypoxemia (O2 saturation<90% on room air or pO2<60 mmHg); fever greater than 38° C. oral (>38.5° C. rectally or tympanically) or hypothermia (<35° C.); white blood cell (WBC) count greater than 10,000 cells/mm3 or less than 4,500 cells/mm3; and greater than 15% immature neutrophils (bands) irrespective of WBC count; and III. PORT score greater than 70 and less than or equal to 130 (i.e., PORT Risk Class III or IV).

3. The subject required initial hospitalization, or treatment in an emergency room or urgent care setting, by the standard of care.

4. The subject's infection required initial treatment with IV antimicrobials.

5. Female subjects of child-bearing potential, and those who were fewer than 2 years postmenopausal, agreed to and complied with using highly effective methods of birth control (i.e. condom plus spermicide, combined oral contraceptive, implant, injectable, indwelling intrauterine device, sexual abstinence, or a vasectomized partner) while participating in this study.

6. Subjects provided written informed consent and demonstrated willingness and ability to comply with all study procedures.

The following criteria were used for exclusion:

1. A PORT score less than or equal to 70 (PORT Risk Class I or II), PORT score greater than 130 (PORT Risk Class V), or required admission to an intensive care unit.

2. CAP suitable for outpatient therapy with an oral antimicrobial agent.

3. Confirmed or suspected respiratory tract infections attributable to sources other than community-acquired bacterial pathogens (e.g., ventilator-associated pneumonia; hospital-acquired pneumonia; visible/gross aspiration pneumonia; suspected viral, fungal, or mycobacterial infection of the lung).

4. Non-infectious causes of pulmonary infiltrates (e.g., pulmonary embolism, chemical pneumonitis from aspiration, hypersensitivity pneumonia, congestive heart failure).

5. Pleural empyema (not including non-purulent parapneumonic effusions).

6. Microbiologically-documented infection with a pathogen known to be resistant to ceftriaxone, or epidemiological or clinical context that suggested high likelihood of a ceftriaxone-resistant "typical" bacterial pathogen (e.g., *Pseudomonas aeruginosa*, methicillin-resistant *Staphylococcus aureus* [MRSA]). Epidemiological clues to potential MRSA infection that included residence in a nursing home or assisted living facility, existence of an ongoing local MRSA infection outbreak, known skin colonization with MRSA, recent skin or skin structure infection due to MRSA, intravenous drug use, and concomitant influenza. Subjects with risk factors for MRSA infection who had predominance of gram-positive cocci in clusters on sputum Gram's stain were to be excluded.

7. Infection with an atypical organism (*M. pneumoniae, C. pneumoniae, Legionella* spp.) was confirmed or suspected based upon the epidemiological context, or infection with *Legionella pneumophila* was confirmed by the urinary antigen test at baseline.

8. Previous treatment with an antimicrobial for CAP within 96 hours leading up to randomization.

The following exceptions were applied: Subjects may have been eligible despite prior antimicrobial therapy if they met the following conditions: either a single dose of an oral or intravenous short-acting antibiotic for CAP or both of the following: unequivocal clinical evidence of treatment failure (e.g. worsening signs and symptoms) following at least 48 hours of prior systemic antimicrobial therapy and isolation of an organism resistant to the prior, systemic, antimicrobial therapy 9. Failure of ceftriaxone (or other third-generation cephalosporin) as therapy for this episode of CAP or prior isolation of an organism associated with this episode of CAP and resistant in vitro to ceftriaxone 10. History of any hypersensitivity or allergic reaction to any β-lactam antimicrobial 11. Past or current history of epilepsy or seizure disorder. Exceptions: well-documented febrile seizure of childhood.

12. Requirement for concomitant antimicrobial or systemic antifungal therapy for any reason. Exceptions: Topical antifungal or antimicrobial therapy, a single oral dose of any antifungal for treatment of vaginal candidiasis.

13. Neoplastic lung disease, cystic fibrosis, progressively fatal disease, chronic neurological disorder preventing clearance of pulmonary secretions, or life expectancy of less than or equal to 3 months.

14. Probenecid administration within 3 days prior to initiation of study drug therapy or requirement for concomitant therapy with probenecid.

15. Infections or conditions that required concomitant systemic corticosteroids. Exceptions: The corticosteroid dose equivalent was less than 40 mg prednisone per day.

16. Severely impaired renal function (CrCl≤30 mL/min) estimated by the Cockroft-Gault formula.

17. Evidence of significant hepatic, hematological, or immunologic disease determined by the following: known acute viral hepatitis; aspartate amino transferase (AST) or alanine aminotransferase (ALT) level greater than 10-fold the upper limit of normal or total bilirubin greater than 3-fold the upper limit of normal; manifestations of end-stage liver disease, such as ascites or hepatic encephalopathy; neutropenia, defined as less than 500 neutrophils/mm3, that was current or anticipated; thrombocytopenia with platelet count less than 60,000 cells/mm3; known infection with human immunodeficiency virus and either a CD4 count less than or equal to 200 cells/mm3 at the last measurement or diagnosis of another Acquired Immune Deficiency and syndrome-defining illness that was current.

18. Evidence of immediately life-threatening disease that was current or impending, including, but not limited to, respiratory failure, acute heart failure, shock, acute coronary syndrome, unstable arrhythmias, hypertensive emergency, acute hepatic failure, active gastrointestinal bleeding, profound metabolic abnormalities (e.g., diabetic ketoacidosis), or acute cerebrovascular events.

19. Residence in a nursing home or assisted living facility that provided 24-hour medical supervision (not including extended living facilities for ambulatory elderly persons) or hospitalization within the 14 days before the onset of symptoms (i.e., healthcare-associated pneumonia).

20. Women who were pregnant or nursing.

21. Participated in any study involving administration of an investigational agent or device within 30 days before randomization into this study or previously participated in the current study.

22. Previous participation in a study of ceftaroline.

23. Unable or unwilling to adhere to the study-specified procedures and restrictions 24. Any condition that, in the opinion of the Investigator, would have compromised the safety of the subject or the quality of the data.

Study Drug: Ceftaroline fosamil was administered in two consecutive 300 mg intravenous (IV) infusions over 30 minutes, every 12 hours (q12h). The 600-mg dose of ceftaroline fosamil infused over 60 minutes was split into two infusions in order to maintain the blind. For subjects with moderate renal impairment (30 ml/min<CrCl≤50 ml/min), as estimated by the Cockroft-Gault formula, unblinded pharmacy staff or unblinded study staff could adjust the dose of ceftaroline fosamil to two consecutive 200 mg infusions and readjust dose to two 300 mg infusions when renal function improved (CrCl>50 mL/min). The duration of treatment was between 5 to 7 days.

Reference Drug:

Ceftriaxone was administered as a 1 g IV infusion over 30 minutes followed by IV saline placebo infused over 30 minutes, every 24 hours (q24h). Twelve hours after each dose of ceftriaxone and saline placebo (i.e., between ceftriaxone doses), subjects received two consecutive saline placebo infusions, each infused over 30 minutes every 24 hours in order to maintain the blind.

The following criteria were used for evaluation: The primary efficacy outcome measures were the per-subject clinical cure rate at test-of-cure (TOC) in the CE and MITTE Populations. Subjects were considered clinically cured at TOC if they had total resolution of all signs and symptoms of the baseline infection, or improvement of the infection such that no further antimicrobial therapy was necessary.

The secondary efficacy outcome measures were:

Per-subject clinical cure rate at EOT in the MITTE and CE Populations;

Per-subject microbiological favorable outcome (eradication or presumed eradication) rate at TOC in the mMITT, mMITTE, and ME Populations;

Overall (combined clinical and radiographic) success rate at TOC in the MITTE and CE Populations;

Per-pathogen clinical cure rate and favorable microbiological outcome rate at TOC in the mMITTE and ME Populations;

Per-subject relapse rate at LFU in the subset of subjects in the CE and MITTE Populations who were clinically cured at TOC; and Per-subject reinfection or recurrence rate at LFU in the subset of subjects in the mMITTE and ME Populations who had a favorable clinical or microbiological outcome (eradication or presumed eradication) at TOC.

All subjects who received any amount of study drug were included in the safety analysis. Safety measures included monitoring for adverse events (AE) up to TOC and serious adverse events (SAE) through LFU; recording vital signs, physical examination, electrocardiogram (ECG), and clinical laboratory findings (clinical chemistry, hematology, and urinalysis), at prespecified times throughout the study.

Efforts were made to obtain pharmacokinetic (PK) samples from approximately 120 to 140 subjects treated with ceftaroline or ceftriaxone on Study Day 3. The PK samples were collected for both the ceftaroline and ceftriaxone groups for the purpose of maintaining the blind, but only PK samples from subjects in the ceftaroline group were analyzed (using a validated assay) by an unblinded central bioanalytical laboratory.

The primary objective of this study was to determine the non-inferiority in the clinical cure rate for ceftaroline compared with that for ceftriaxone at TOC in the CE and MITTE Populations in adult subjects with CAP.

There were seven study populations, six of which were statistically analyzed.

1. The intent-to-treat (ITT) Population included all randomized subjects and was not analyzed.
2. The MITT Population included all randomized subjects who received any amount of the study drug.
3. The MITTE Population consisted of all subjects in the MITT Population in PORT Risk Class III or IV.
4. The mMITT Population consisted of all subjects in the MITT Population who met the minimal disease criteria for CAP and who had at least one typical bacterial organism consistent with a CAP pathogen identified from an appropriate microbiological specimen (e.g., blood, sputum, pleural fluid). Subjects with *Mycoplasma pneumoniae* or *Chlamydophila pneumoniae* as the sole causative pathogen of infection, and all subjects with *L. pneumophila* infection were excluded from the mMITT Population.
5. The mMITTE Population consisted of subjects in the mMITT Population but excluded subjects in PORT Risk Class II.
6. The CE Population consisted of all subjects in the MITTE Population who met all evaluability criteria and for whom sufficient information regarding the CAP was available to determine the subject's outcome (i.e., the subject did not have an indeterminate outcome).
7. The ME Population was a subset of the CE and mMITTE Populations and included each subject in the CE Population who also had at least one "typical" bacterial pathogen has been isolated from an appropriate microbiological specimen.

A two-sided 95% confidence interval (CI) for the observed difference in the primary outcome measure (clinical cure rate) between the ceftaroline group and the ceftriaxone group was calculated for those subjects with PORT Risk Class III or IV. Non-inferiority was concluded if the lower limit of the 95% CI was higher than −10%.

Assuming a point estimate for the clinical cure rate in the CE Population of 90% in the ceftriaxone group, and 90% in the ceftaroline group, a non-inferiority margin of 10%, a power of 90% and 25% non-evaluability rate, and that about 76 subjects in PORT Risk Class II were enrolled, a total sample size of 626 subjects was required (313 subjects in each treatment group).

Secondary efficacy outcomes were analyzed by determining two-sided 95% CIs for the observed difference in the outcome rates between the ceftaroline group and the ceftriaxone group for those subjects in PORT Risk Class III and IV.

TABLE 6

Population Distribution

| Disposition | Population | Ceftaroline | Ceftriaxone | Total |
| --- | --- | --- | --- | --- |
| By Population | | | | |
| Randomized | ITT | 317 | 310 | 627 |
| Received Study Drug | MITT | 315 | 307 | 622 |
| PORT III or IV | MITTE | 289 | 273 | 562 |
| Had clinical outcome assessment | CE | 235 | 215 | 450 |
| Had Baseline Pathogen | mMITTE | 90 | 88 | 178 |
| Had baseline pathogen and clinical outcome assessment | ME | 85 | 76 | 161 |
| By Withdrawal | MITTE | 289 | 273 | 562 |
| Completed Study | | 259 (89.6) | 248 (90.8) | 507 (90.2) |
| Withdrew from Study | | 30 (10.4) | 25 (9.2) | 55 (9.8) |

TABLE 6-continued

Population Distribution

| Disposition | Population Ceftaroline | Ceftriaxone | Total |
|---|---|---|---|
| Reason for early withdrawal | | | |
| Adverse Event | 8 (2.8) | 7 (2.6) | 15 (2.7) |
| Noncompliance with study treatment | 0 | 1 (0.4) | 1 (0.2) |
| At the request of the sponsor/investigator | 1 (0.3) | 1 (0.4) | 2 (0.4) |
| Withdrew Consent | 4 (1.4) | 8 (2.9) | 12 (2.1) |
| Lost to Follow-Up | 16 (5.5) | 8 (2.9) | 24 (4.3) |
| Other | 1 (0.3) | 0 | 1 (0.2) |

Demographics: In the MITTE population, subjects were predominantly male (62%), non-Hispanic (84%), white (96%), and had a mean age of approximately 61 years. Most subjects had a PORT score of III (59% in the ceftaroline group, 63% in the ceftriaxone group). The number of subjects with any relevant medical history was 51% in the ceftaroline group and 44% in the ceftriaxone group. The most common relevant medical history was structural lung disease (33% in the ceftaroline group and 32% in the ceftriaxone group).

Treatment groups were well balanced with regards to the pathogenic organisms identified from respiratory and blood cultures, or urinary antigen tests. The most common pathogens were *Streptococcus pneumoniae* and *Staphylococcus aureus*. The most common gram-negative pathogens were *Haemophilus influenzae, H. parainfluenzae*, and *Klebsiella pneumoniae*. The incidence of bacteremia was similar between the two treatment groups (5.2% ceftaroline; 4.0% ceftriaxone).

Demographics and baseline characteristics in the CE population were similar to those in the MITTE Population.

TABLE 7

Efficacy results

| Population | Ceftaroline n (%) | Ceftriaxone n (%) | Difference$^a$ | 95% CI$^b$ |
|---|---|---|---|---|
| Clinical Success at the TOC Visit—Noninferiority (CE and MITTE Populations) | | | | |
| CE, N | 235 | 215 | | |
| | 193 (82.1) | 166 (77.2) | 4.9 | (−2.5, 12.5) |
| MITTE, N | 289 | 273 | | |
| | 235 (81.3) | 206 (75.5) | 5.9 | (−1.0, 12.7) |
| Favorable$^d$ Microbiological Outcome at the TOC Visit (ME and mMITTE Populations) | | | | |
| ME, N | 85 | 76 | | |
| | 72 (84.7) | 63 (82.9) | 1.8 | (−9.7, 13.7) |
| mMITTE, N | 90 | 88 | | |
| | 74 (82.2) | 72 (81.8) | 0.4 | (−11.1, 11.9) |
| Per-subject Clinical Cure Rates at the EOT Visit (CE and MITTE Populations) | | | | |
| CE, N | 235 | 215 | | |
| | 202 (86.0) | 172 (80.0) | 6.0 | (−1.0, 13.0) |
| MITTE, N | 289 | 273 | | |
| | 249 (86.2) | 215 (78.8) | 7.4 | (1.1, 13.8) |

Abbreviations:
CE = clinically evaluable;
EOT = end-of-therapy;
ME = microbiologically evaluable;
CI = confidence interval;
MITT = modified intent-to-treat;
mMITTE = modified microbiologicalintent-to-treat with PORT score III or IV.
$^a$Difference = % cures in the ceftaroline group minus % cures in the ceftriaxone group.
$^b$CIs were calculated using the Miettinen and Nurminen method without adjustment.
$^c$Favorable responses included eradication and presumed eradication.

The data provided in Table 7 establishes that ceftaroline and prodrugs thereof (e.g., ceftaroline fosamil) are surprisingly and unexpectedly effective for the treatment of community acquired pneumonia.

TABLE 8

Clinical Cure Rates and Favorable Microbiological Outcome by baseline pathogen

| Pathogen | Ceftaroline (N=) | Ceftriaxone (N=) |
|---|---|---|
| Clinical Cure Rates at the TOC Visit by Baseline Pathogen (ME Population) | | |
| S. pneumoniae | 33/39 (84.6) | 23/32 (71.9) |
| MDRSP | 2/2 (100.0) | 1/4 (25.0) |
| S. aureus | 10/15 (66.7) | 8/15 (53.3) |
| H. influenzae | 13/15 (86.7) | 11/12 (91.7) |
| H. parainfluenzae | 9/9 (100.0) | 6/7 (85.7) |
| K. pneumoniae | 6/6 (100.0) | 7/8 (87.5) |
| Favorable Microbiological Outcome at TOC by Baseline Pathogen (ME) | | |
| S. pneumoniae | 35/39 (89.7) | 25/32 (78.1) |
| MDRSP | 2/2 (100.0) | 2/4 (50.0) |
| S. aureus | 11/15 (73.3) | 11/15 (73.3) |
| H. influenzae | 13/15 (86.7) | 11/12 (91.7) |
| H. parainfluenzae | 9/9 (100.0) | 7/7 (100.0) |
| K. pneumoniae | 6/6 (100.0) | 7/8 (87.5) |

The data provided in Table 8 establishes that ceftaroline and prodrugs thereof (e.g., ceftaroline fosamil) are surprisingly and unexpectedly effective for the treatment of community acquired pneumonia.

A higher percentage of subjects in the ceftaroline treatment group were reported to have had treatment emergent adverse events (TEAEs) (53.7% ceftaroline; 47.2% ceftriaxone) but similar percentages were reported to have any study-drug-related TEAEs (12.4% ceftaroline; 13.7% ceftriaxone) in the two treatment groups. The incidence of subjects with any SAEs were also similar in the two treatment groups (13.0% ceftaroline; 12.7% ceftriaxone), as were the incidences of subjects with TEAEs leading to premature discontinuation from study drug administration (0.6% ceftaroline; 1.3% ceftriaxone). The incidence of deaths was comparable between the two treatment arms (2.9% ceftaroline; 2.0% ceftriaxone). The most common TEAEs (occurring in 2% or more of subjects) in either treatment group are shown below. Adverse Events Reported Incidence >=2% of Subjects in Any Treatment Group: Safety Population

TABLE 9

Adverse events

| Adverse Event (MedDRA Preferred Term) | Ceftaroline (N = 315) Number (%) of Subjects | Ceftriaxone (N = 307) |
|---|---|---|
| Any AE | 169 (53.7) | 145 (47.2) |
| Diarrhea | 12 (3.8) | 9 (2.9) |
| Nausea | 6 (1.9) | 6 (2.0) |
| Pneumonia | 8 (2.5) | 4 (1.3) |
| Hypokalemia | 10 (3.2) | 5 (1.6) |
| Head ache | 11 (3.5) | 5 (1.6) |
| Insomnia | 10 (3.2) | 8 (2.6) |
| COPD | 8 (2.5) | 5 (1.6) |
| Pleural effusion | 4 (1.3) | 7 (2.3) |
| Phlebitis | 10 (3.2) | 8 (2.6) |
| Hypertension | 8 (2.5) | 8 (2.6) | a "Any AE" includes subjects who reported at least one adverse event.

There were no TEAEs with incidences in the two treatment groups differing by 2% or more.

The study-drug-related TEAEs occurring in 1.0% or more of subjects in either treatment group were diarrhea (1.9% ceftaroline; 2.0% ceftriaxone), nausea (0.6% ceftaroline; 1.6% ceftriaxone), blood creatinine phosphokinase increased (1.3% ceftaroline; 0.7% ceftriaxone), alanine aminotransferase increased (0.3% ceftaroline; 1.0% ceftriaxone), headache (0.6% ceftaroline; 1.0% ceftriaxone) and phlebitis (2.9% ceftaroline; 1.6% ceftriaxone)

TEAEs that were no more than mild (28.9% ceftaroline; 19.9% ceftriaxone) were more frequent in the ceftaroline treatment group. TEAEs that were no more than moderate (18.4% ceftaroline; 19.9% ceftriaxone) or severe were experienced by similar percentages of subjects in both treatment groups (6.3% ceftaroline; 7.5% ceftriaxone).

Two subjects (1 in ceftaroline, 1 in ceftriaxone) had SAEs considered to be possibly or probably related to study drug (convulsion for the subject in the ceftaroline group; hepatic enzyme increased for the subject in the ceftriaxone group).

A higher incidence of post baseline Direct Coombs' seroconversion was observed in the ceftaroline group (8.1%) than in the ceftriaxone group (3.8%). No evidence of hemolytic anemia was identified in either group.

Changes in hematology and clinical chemistry parameters observed on therapy were small and similar in the two treatment groups and no laboratory related trends or safety concerns were observed. Review of the potentially clinically significant (PCS) laboratory values showed overall low incidence and no meaningful differences between the treatment groups.

Thus, the present example establishes that ceftaroline and prodrugs thereof (e.g., ceftaroline fosamil) are surprisingly and unexpectedly effective for the treatment of bacterial infections including community acquired pneumonia and cSSSI.

Example 5

A Phase 3, multicenter, randomized, double-blind, comparative study was conducted to evaluate the safety and efficacy of ceftaroline relative to ceftriaxone, with adjunctive clarithromycin, in the treatment of adult subjects with community-acquired pneumonia (CAP).

The primary objective of the study was to determine the non-inferiority in the clinical cure rate for ceftaroline compared with that for ceftriaxone at test-of-cure (TOC) in the clinically evaluable (CE) and modified intent-to-treat efficacy (MITTE) populations in adult subjects with CAP. The secondary objective of the study was to evaluate the following: the clinical response at end-of-therapy (EOT); the microbiological favorable outcome rate at TOC; the overall (clinical and radiographic) success rate at TOC; the clinical and microbiological response by pathogen at TOC; clinical relapse at late follow-up (LFU); microbiological reinfection/recurrence at LFU; and safety.

The intent-to-treat population (ITT) included 305 subjects for ceftaroline and 309 subjects for ceftriaxone while modified intent-to-treat (MITT) or safety population included 299 subjects for ceftaroline and 307 subjects for ceftriaxone.

The following populations were analyzed for efficacy:
1. MITTE population; 291 (ceftaroline) and 300 (ceftriaxone)
2. CE population; 224 (ceftaroline) and 234 (ceftriaxone)
3. Microbiological modified intent-to-treat (mMITT) population; 75 (ceftaroline) and 82 (ceftriaxone)
4. Microbiological modified intent-to-treat efficacy (mMITTE) population: 75 (ceftaroline) and 80 (ceftriaxone)
5. Microbiologically evaluable (ME) population: 69 (ceftaroline) and 71 (ceftriaxone) The following inclusion criteria were used:
1. Subjects were males and females 18 or more years of age
2. Subjects had community-acquired pneumonia meeting the following criteria:
I. Radiographically confirmed pneumonia (new or progressive pulmonary infiltrate(s) on chest radiograph [CXR] or chest computed tomography [CT] scan consistent with bacterial pneumonia); and
II. Acute illness (<7 days' duration) with at least three of the following clinical signs or symptoms consistent with a lower respiratory tract infection: new or increased cough; purulent sputum or change in sputum character; auscultatory findings consistent with pneumonia (e.g., rales, egophony, findings of consolidation); dyspnea, tachypnea, or hypoxemia (O2 saturation<90% on room air or pO2<60 mmHg); fever greater than 38° C. oral (>38.5° C. rectally or tympanically) or hypothermia (<35° C.); white blood cell (WBC) count greater than 10,000 cells/mm3 or less than 4,500 cells/mm3; greater than 15% immature neutrophils (bands) irrespective of WBC count; and
III. PORT score greater than 70 and less than or equal to 130 (i.e., PORT Risk Class III or IV).
3. The subject required initial hospitalization, or treatment in an emergency room or urgent care setting, by the standard of care.
4. The subject's infection required initial treatment with IV antimicrobials.
5. Female subjects of child-bearing potential, and those who were fewer than 2 years postmenopausal, agreed to and complied with using highly effective methods of birth control (i.e., condom plus spermicide, combined oral contraceptive, implant, injectable, indwelling intrauterine device, sexual abstinence, or a vasectomized partner) while participating in this study
6. Subjects provided written informed consent and demonstrated willingness and ability to comply with all study procedures.

The exclusion criteria were:

1. A PORT score less than or equal to 70 (PORT Risk Class I or II), PORT score greater than 130 (PORT Risk Class V), or required admission to an intensive care unit.

2. CAP suitable for outpatient therapy with an oral antimicrobial agent.

3. Confirmed or suspected respiratory tract infections attributable to sources other than community-acquired bacterial pathogens (e.g., ventilator-associated pneumonia; hospital-acquired pneumonia; visible/gross aspiration pneumonia; suspected viral, fungal, or mycobacterial infection of the lung).

4. Non-infectious causes of pulmonary infiltrates (e.g., pulmonary embolism, chemical pneumonitis from aspiration, hypersensitivity pneumonia, congestive heart failure).

5. Pleural empyema (not including non-purulent parapneumonic effusions).

6. Microbiologically-documented infection with a pathogen known to be resistant to ceftriaxone, or epidemiological or clinical context that suggested high likelihood of a ceftriaxone-resistant "typical" bacterial pathogen (eg, *Pseudomonas aeruginosa*, methicillin-resistant *Staphylococcus aureus* [MRSA]). Epidemiological clues to potential MRSA infection that included residence in a nursing home or assisted living facility, existence of an ongoing local MRSA infection outbreak, known skin colonization with MRSA, recent skin or skin structure infection due to MRSA, intravenous drug use, and concomitant influenza. Subjects with risk factors for MRSA infection who had predominance of gram-positive cocci in clusters on sputum Gram's stain were to be excluded.

7. Infection with an atypical organism (*M. pneumoniae, C. pneumoniae, Legionella* spp.) was confirmed or suspected based upon the epidemiological context, or infection with *Legionella pneumophila* was confirmed by the urinary antigen test at baseline.

8. Previous treatment with an antimicrobial for CAP within 96 hours leading up to randomization.

Exceptions: Subjects may have been eligible despite prior antimicrobial therapy if they met the following conditions: either a single dose of an oral or intravenous short-acting antibiotic for CAP or both of the following: unequivocal clinical evidence of treatment failure (eg, worsening signs and symptoms) following at least 48 hours of prior systemic antimicrobial therapy and isolation of an organism resistant to the prior, systemic, antimicrobial therapy.

9. Failure of ceftriaxone (or other third-generation cephalosporin) as therapy for this episode of CAP or prior isolation of an organism associated with this episode of CAP and resistant in vitro to ceftriaxone.

10. History of any hypersensitivity or allergic reaction to any β-lactam antimicrobial.

11. History of any hypersensitivity or allergic reaction to clarithromycin or any macrolide/ketolide.

12. Inability to take oral clarithromycin.

13. Requirement for concomitant therapy with any drug known to exhibit a contraindicated drug-drug interaction with clarithromycin; or labeled contraindication to use of clarithromycin.

14. Past or current history of epilepsy or seizure disorder. Exceptions: well-documented febrile seizure of childhood.

15. Requirement for concomitant antimicrobial or systemic antifungal therapy for any reason. Exceptions: Topical antifungal or antimicrobial therapy, a single oral dose of any antifungal for treatment of vaginal candidiasis.

16. Neoplastic lung disease, cystic fibrosis, progressively fatal disease, chronic neurological disorder preventing clearance of pulmonary secretions, or life expectancy of less than or equal to 3 months.

17. Probenecid administration within 3 days prior to initiation of study drug therapy or requirement for concomitant therapy with probenecid.

18. Infections or conditions that required concomitant systemic corticosteroids. Exceptions: The corticosteroid dose equivalent was less than 40 mg prednisone per day 19. Severely impaired renal function (CrCl≤30 mL/min) estimated by the Cockroft-Gault formula 20. Evidence of significant hepatic, hematological, or immunologic disease determined by the following: known acute viral hepatitis; aspartate amino transferase (AST) or alanine aminotransferase (ALT) level greater than 10-fold the upper limit of normal or total bilirubin greater than 3-fold the upper limit of normal; manifestations of end-stage liver disease, such as ascites or hepatic encephalopathy; neutropenia, defined as less than 500 neutrophils/mm3, that was current or anticipated; thrombocytopenia with platelet count less than 60,000 cells/mm3; known infection with human immunodeficiency virus and either a CD4 count less than or equal to 200 cells/mm3 at the last measurement or diagnosis of another Acquired Immune Deficiency Syndrome defining illness that was current.

21. Evidence of immediately life-threatening disease that was current or impending, including, but not limited to, respiratory failure, acute heart failure, shock, acute coronary syndrome, unstable arrhythmias, hypertensive emergency, acute hepatic failure, active gastrointestinal bleeding, profound metabolic abnormalities (eg, diabetic ketoacidosis), or acute cerebrovascular events.

22. Residence in a nursing home or assisted living facility that provided 24-hour medical supervision (not including extended living facilities for ambulatory elderly persons) or hospitalization within the 14 days before the onset of symptoms (i.e., healthcare-associated pneumonia).

23. Women who were pregnant or nursing.

24. Participated in any study involving administration of an investigational agent or device within 30 days before randomization into this study or previously participated in the current study.

25. Previous participation in a study of ceftaroline.

26. Unable or unwilling to adhere to the study-specified procedures and restrictions.

27. Any condition that, in the opinion of the Investigator, would have compromised the safety of the subject or the quality of the data.

Study drug: Ceftaroline fosamil was administered in two consecutive 300 mg intravenous (IV) infusions over 30 minutes, every 12 hours (q12h). The 600-mg dose of ceftaroline fosamil infused over 60 minutes was split into two infusions in order to maintain the blind. For subjects with moderate renal impairment (30 mL/min<CrCl≤50 mL/min), as estimated by the Cockroft-Gault formula, unblinded pharmacy staff or unblinded study staff could adjust the dose of ceftaroline fosamil to two consecutive 200 mg infusions and readjust dose to two 300 mg infusions when renal function improved (CrCl>50 mL/min). The duration of treatment was between 5 to 7 days.

Reference drug: Ceftriaxone was administered as a 1 g IV infusion over 30 minutes followed by IV saline placebo infused over 30 minutes, every 24 hours (q24h). Twelve hours after each dose of ceftriaxone and saline placebo (i.e., between ceftriaxone doses), subjects received two consecutive saline placebo infusions, each infused over 30 minutes every 24 hours (q24h) in order to maintain the blind.

All subjects initially received two doses (500 mg every 12 hours) of oral adjunctive therapy with clarithromycin following randomization.

The primary efficacy outcome measures were the per-subject clinical cure rate at TOC in the CE and MITTE Populations. Subjects were considered clinically cured at TOC if they had total resolution of all signs and symptoms of the baseline infection, or improvement of the infection such that no further antimicrobial therapy was necessary.

The secondary efficacy outcome measures were:

Per-subject clinical cure rate at EOT in the MITTE and CE Populations;

Per-subject microbiological favorable outcome (eradication or presumed eradication) rate at TOC in the mMITT, mMITTE, and ME Populations;

Overall (combined clinical and radiographic) success rate at TOC in the MITTE and CE Populations;

Per-pathogen clinical cure rate and favorable microbiological outcome rate at TOC in the mMITTE and ME Populations;

Per-subject relapse rate at LFU in the subset of subjects in the CE and MITTE Populations who were clinically cured at TOC; and Per-subject reinfection or recurrence rate at LFU in the subset of subjects in the mMITTE and ME Populations who had a favorable clinical or microbiological outcome (eradication or presumed eradication) at TOC.

All subjects who received any amount of study drug were included in the safety analysis. Safety measures included monitoring for adverse events (AE) up to TOC and serious adverse events (SAE) through LFU; recording vital signs, physical examination, electrocardiogram (ECG), and clinical laboratory findings (clinical chemistry, hematology, and urinalysis), at prespecified times throughout the study.

Efforts were made to obtain pharmacokinetic (PK) samples from approximately 120 to 140 subjects treated with ceftaroline or ceftriaxone on Study Day 3. The PK samples were collected for both the ceftaroline and ceftriaxone groups for the purpose of maintaining the blind, but only PK samples from subjects in the ceftaroline group were analyzed (using a validated assay) by an unblinded central bioanalytical laboratory.

The primary objective of this study was to determine the non-inferiority in the clinical cure rate for ceftaroline compared with that for ceftriaxone at TOC in the CE and MITTE Populations in adult subjects with CAP.

There were seven study populations, six of which were statistically analyzed.

1. The ITT Population included all randomized subjects and was not analyzed.

2. The MITT Population included all randomized subjects who received any amount of the study drug.

3. The MITTE Population consisted of all subjects in the MITT Population in PORT Risk Class III or IV.

4. The mMITT Population consisted of all subjects in the MITT Population who met the minimal disease criteria for CAP and who had at least one typical bacterial organism consistent with a CAP pathogen identified from an appropriate microbiological specimen (e.g. blood, sputum, pleural fluid). Subjects with *Mycoplasma pneumoniae* or *Chlamydophila pneumoniae* as the sole causative pathogen of infection, and all subjects with *L. pneumophila* infection were excluded from the mMITT Population.

5. The mMITTE Population consisted of subjects in the mMITT Population but excluded subjects in PORT Risk Class II.

6. The CE Population consisted of all subjects in the MITTE Population who met all evaluability criteria and for whom sufficient information regarding the CAP was available to determine the subject's outcome (i.e., the subject did not have an indeterminate outcome).

7. The ME Population was a subset of the CE and mMITTE Populations and included each subject in the CE Population who also had at least one "typical" bacterial pathogen has been isolated from an appropriate microbiological specimen.

A two-sided 95% confidence interval (CI) for the observed difference in the primary outcome measure (clinical cure rate) between the ceftaroline group and the ceftriaxone group was calculated for those subjects with PORT Risk Class III or IV. Non-inferiority was concluded if the lower limit of the 95% CI was higher than −10%. Assuming a point estimate for the clinical cure rate in the CE Population of 90% in the ceftriaxone group, and 90% in the ceftaroline group, a non-inferiority margin of 10%, a power of 90% and 25% non-evaluability rate, and that about 76 subjects in PORT Risk Class II were enrolled, a total sample size of 626 subjects was required (313 subjects in each treatment group).

Secondary efficacy outcomes were analyzed by determining two-sided 95% CIs for the observed difference in the outcome rates between the ceftaroline group and the ceftriaxone group for those subjects in PORT Risk Class III and IV.

TABLE 10

Population distribution

| Disposition | Population | Ceftaroline | Ceftriaxone | Total |
|---|---|---|---|---|
| By population | | | | |
| Randomized | ITT | 305 | 309 | 614 |
| Received Study Drug | MITT | 299 | 307 | 606 |
| PORT III or IV | MITTE | 291 | 300 | 591 |
| Had clinical outcome assessment | CE | 224 | 234 | 458 |
| Had Baseline Pathogen | mMITTE | 75 | 80 | 155 |
| Had baseline pathogen and clinical outcome assessment | ME | 69 | 71 | 140 |
| By Withdrawal | MITTE | 291 | 300 | 591 |
| Completed Study | | 268 (92.1) | 276 (92.0) | 544 (92.0) |
| Withdrew from Study | | 23 (7.9) | 24 (8.0) | 47 (8.0) |
| Reason for early withdrawal | | | | |
| Adverse Event | | 5 (1.7) | 7 (2.3) | 12 (2.0) |
| At the request of the sponsor/investigator | | 1 (0.3) | 0 | 1 (0.2) |
| Withdrew Consent | | 9 (3.1) | 6 (2.0) | 15 (2.5) |
| Lost to Follow-Up | | 7 (2.4) | 10 (3.3) | 17 (2.9) |
| Other | | 1 (0.3) | 1 (0.3) | 2 (0.3) |

Demographics: In the MITTE population, subjects were predominantly male (64%), non-Hispanic (91%), and white (89%), and had a mean age of approximately 61 years. Most subjects had a PORT score of III (65% in the ceftaroline group, 61% in the ceftriaxone group). The number of subjects with any relevant medical history was 42% in the ceftaroline group and 37% in the ceftriaxone group. The most common relevant medical history was structural lung disease (22% in the ceftaroline group; 20% in the ceftriaxone group).

Treatment groups were well balanced with regards to the pathogenic organisms identified from respiratory and blood cultures, or urinary antigen tests. The most common pathogens were *Streptococcus pneumoniae* and *Staphylococcus aureus*. The most common gram-negative pathogens were *Haemophilus parainfluenzae, H. influenzae,* and *Escherichia coli*. The incidence of bacteremia was similar between the two treatment groups (2.7% ceftaroline; 3.0% ceftriaxone). Demographics and baseline characteristics in the CE population were similar to those in the MITTE Population.

TABLE 11

Efficacy Results

| Population | Ceftaroline n (%) | Ceftriaxone n (%) | Difference[a] | 95% CI[b] |
|---|---|---|---|---|
| Clinical Success at the TOC Visit—Noninferiority (CE and MITTE Populations) | | | | |
| CE, N | 224 | 234 | | |
|  | 194 (86.6) | 183 (78.2) | 8.4 | (1.4, 15.4) |
| MITTE, N | 291 | 300 | | |
|  | 244 (83.8) | 233 (77.7) | 6.2 | (−0.2, 12.6) |
| Favorable[d] Microbiological Outcome at the TOC Visit (ME and mMITTE Populations) | | | | |
| ME, N | 69 | 71 | | |
|  | 62 (89.9) | 56 (78.9) | 11.0 | (−1.2, 23.3) |
| mMITTE, N | 75 | 80 | | |
|  | 66 (88.0) | 63 (78.8) | 9.3 | (−2.7, 21.1) |
| Per-subject Clinical Cure Rates at the EOT Visit (CE and MITTE Populations) | | | | |
| CE, N | 224 | 234 | | |
|  | 197 (87.9) | 188 (80.3) | 7.6 | (0.9, 14.3) |
| MITTE, N | 291 | 300 | | |
|  | 253 (86.9) | 242 (80.7) | 6.3 | (0.3, 12.3) |

Abbreviations:
CE = clinically evaluable;
EOT = end-of-therapy;
ME = microbiologically evaluable;
CI = confidence interval;
MITT = modified intent-to-treat;
mMITTE = modified microbiological intent-to-treat with PORT score III or IV.
[a]Difference = % cures in the ceftaroline group minus % cures in the ceftriaxone group.
[b]CIs were calculated using the Miettinen and Nurminen method without adjustment.
[c]Favorableresponses included eradication and presumed eradication.

The data provided in Table 11 establishes that ceftaroline and prodrugs thereof (e.g., ceftaroline fosamil) are surprisingly and unexpectedly effective for the treatment of community acquired pneumonia.

TABLE 12

Clinical Cure Rates and Favorable Microbiological Outcome at TOC by Baseline Pathogen

| Pathogen | Ceftaroline N = 69 | Ceftriaxone N = 71 |
|---|---|---|
| Clinical Cure Rates at the TOC Visit by Baseline Pathogen (ME Population) | | |
| S. pneumoniae | 21/24 (87.5) | 18/27 (66.7) |
| MDRSP | 2/2 (100.0) | 0 |
| S. aureus | 8/10 (80.0) | 7/12 (58.3) |
| H. parainfluenzae | 7/7 (100.0) | 9/10 (90.0) |
| H. influenzae | 2/3 (66.7) | 6/8 (75.0) |
| E. coli | 8/8 (100.0) | 5/6 (83.3) |
| Favorable Microbiological Outcome at TOC by Baseline Pathogen (ME) | | |
| S. pneumoniae | 21/24 (87.5) | 18/27 (66.7) |
| MDRSP | 2/2 (100.0) | 0 |
| S. aureus | 8/10 (80.0) | 8/12 (66.7) |
| H. parainfluenzae | 7/7 (100.0) | 9/10 (90.0) |
| H. influenzae | 2/3 (66.7) | 6/8 (75.0) |
| E. coli | 8/8 (100.0) | 6/6 (100.0) |

The data provided in Table 12 establishes that ceftaroline and prodrugs thereof (e.g., ceftaroline fosamil) are surprisingly and unexpectedly effective for the treatment of community acquired pneumonia.

The percentage of subjects experiencing treatment-emergent adverse events (TEAEs) was lower in the ceftaroline group (39.9%) compared with the ceftriaxone group (44.2%); however the percentage of TEAEs assessed as drug related by the Investigators was higher in the ceftaroline group (17.1%) compared with the ceftriaxone group (12.7%). The incidence of subjects with any SAEs were similar in the two treatment groups (9.4% ceftaroline; 10.7% ceftriaxone), as was the incidence of subjects with TEAEs leading to premature discontinuation from study drug administration (3.7% ceftaroline; 3.9% ceftriaxone). The percentage of deaths was comparable between the two treatment groups (1.7% ceftaroline; 2.6% ceftriaxone). The most common TEAEs (occurring in 2% or more of subjects) in either treatment group are shown below. Adverse Events Reported Incidence >=2% of Subjects in Any Treatment Group: Safety Population

TABLE 13

Adverse Events

| Adverse Event | Number (%) of Subjects | |
|---|---|---|
| (MedDRA Preferred Term) | Ceftaroline (N = 298) | Ceftriaxone (N = 308) |
| Any AE | 119 (39.9) | 136 (44.2) |
| Diarrhea | 14 (4.7) | 7 (2.3) |
| Nausea | 8 (2.7) | 8 (2.6) |
| Constipation | 7 (2.3) | 5 (1.6) |
| Hypokalemia | 4 (1.3) | 10 (3.2) |
| Headache) | 10 (3.4) | 4 (1.3) |
| Insomnia | 9 (3.0) | 6 (1.9) |
| Phlebitis | 7 (2.3) | 5 (1.6) |
| Hypertension | 6 (2.0) | 8 (2.6) |

"Any AE" includes subjects who reported at least one adverse event.

The only TEAEs with incidences in the two treatment groups differing by 2% or more were diarrhea (4.7% ceftaroline; 2.3% ceftriaxone) and headache (3.4% ceftaroline; 1.3% ceftriaxone). The study-drug-related TEAEs occurring in 1.0% or more of subjects in either treatment group were sinus bradychardia (1.0% ceftaroline; 1.0% ceftriaxone), diarrhea (4.4% ceftaroline; 1.0% ceftriaxone), nausea (1.3% ceftaroline; 0.3% ceftriaxone), hepatic enzyme increased (0.3% ceftaroline; 1.0% ceftriaxone), headache (1.0% ceftaroline; 0.0% ceftriaxone) and phlebitis (1.3% ceftaroline; 0.6% ceftriaxone) TEAEs that were no more than mild (19.8% ceftaroline; 20.1% ceftriaxone) or no more than moderate (13.8% ceftaroline; 16.9% ceftriaxone) were similar or less frequent in the ceftaroline group as compared with the ceftriaxone group. TEAEs that were severe were also experienced by similar percentages of subjects in both treatment groups (6.4% ceftaroline; 7.1% ceftriaxone).

Seven subjects (2 ceftaroline, 5 ceftriaxone) had SAEs considered to be possibly or probably related to study drug. A higher incidence of post baseline Direct Coombs' seroconversion was observed in the ceftaroline group (11.8%) than in the ceftriaxone group (5.2%). No evidence of hemolytic anemia was identified in either group. Changes in hematology and clinical chemistry parameters observed on therapy were small and similar in the two treatment groups and no laboratory related trends or safety concerns were observed. Review of the potentially clinically significant (PCS) laboratory values showed overall low incidence and no meaningful differences between the treatment groups.

The combined data from the two studies in Examples 1 and 2 surprisingly and unexpectedly shows a 6.7% higher clinical cure rate for ceftaroline versus ceftriaxone at test-of-cure (TOC) in the clinically evaluable (CE) population (See Table 14). Furthermore, the combined data shows an 8.7% and 9.7% higher clinical cure rate for ceftaroline versus ceftriaxone in the microbiological modified intent-to-treat efficacy (mMITTE) and microbiologically evaluable (ME) populations, respectively (See Table 14).

TABLE 14

Combined clinical cure rate

| Population | Ceftaroline (%) n/N | Ceftriaxone (%) n/N | Weighted treatment difference (95% CI) |
|---|---|---|---|
| CE | 387/459 (84.3) | 349/449 (77.7) | 6.7 (1.6, 11.8) |
| MITTE | 479/580 (82.6) | 439/573 (76.6) | 6.0 (1.4, 10.7) |
| mMITTE | 138/165 (83.6) | 126/168 (75.0) | 8.7 (−0.0, 17.4) |
| ME | 131/154 (85.1) | 111/147 (75.5) | 9.7 (0.7, 18.8) |

CE = clinically evaluable;
ME = microbiologically evaluable;
MITTE = modified intent-to-treat efficacy;
mMITTE = microbiological modified intent-to-treat efficacy;
TOC = test-of-cure;
95% CI = 95% confidence interval around the treatment difference (CPT-CRO).

Example 6

Ceftaroline fosamil was evaluated in four controlled comparative Phase 3 clinical studies (two in cSSSI and two in CABP). The studies included 1305 adult patients treated with ceftaroline fosamil (600 mg administered intravenously over 1 hour every 12 h) and 1301 patients that received comparator (vancomycin plus aztreonam or ceftriaxone) for a treatment period of up to 21 days. The median age of patients treated with ceftaroline fosamil was 54 years, ranging between 18 and 99 years old. Patients treated with ceftaroline fosamil were predominantly male (63%) and Caucasian (82%).

In four controlled comparative pooled Phase 3 clinical studies, treatment discontinuations due to adverse events occurred in 4% of patients receiving ceftaroline fosamil and 5% of patients receiving comparator drugs with the most common adverse event leading to discontinuation being hypersensitivity for both groups at a rate of 0.3% in ceftaroline fosamil and 0.5% in comparator. Serious adverse events occurred in 8% of patients receiving ceftaroline fosamil and 8% of patients receiving comparator drugs.

No adverse reactions occurred in greater than 5% of patients receiving ceftaroline fosamil. The most common adverse reactions occurring in ≥4% of patients receiving ceftaroline fosamil in the pooled phase 3 clinical studies were diarrhea, nausea, and headache.

TABLE 15

Adverse Reactions Occurring in ≥2% of Patients Receiving ceftaroline fosamil in the four controlled Comparative Phase 3 Clinical Studies

| System Organ Class/ Preferred Term | Ceftaroline fosamil (N = 1305) | Pooled Comparators[a] (N = 1301) |
|---|---|---|
| Gastrointestinal disorders | | |
| Diarrhea | 5% | 3% |
| Nausea | 4% | 4% |
| Constipation | 2% | 2% |
| Vomiting | 2% | 2% |
| Investigations | | |
| Increased transaminases | 2% | 3% |
| Metabolism and nutrition disorders | | |
| Hypokalemia | 2% | 3% |
| Nervous system disorders | | |
| Headache | 4% | 3% |
| Psychiatric disorders | | |
| Insomnia | 3% | 2% |
| Skin and subcutaneous tissue disorders | | |
| Rash | 3% | 2% |
| Pruritus | 2% | 5% |
| Vascular disorders | | |
| Phlebitis | 2% | 1% |

[a]Comparators included vancomycin 1 gram IV q12h plus aztreonam 1 gram IV q12h in the Phase 3 cSSSI studies, and ceftriaxone 1 gram IV q24h in the Phase 3 CABP studies.

Thus, the present examples establish that the present compositions and methods of treatment using ceftaroline or a prodrug thereof (e.g., ceftaroline fosamil) are surprisingly and unexpectedly effective in the treatment of complicated skin and structure infections and community-acquired bacterial pneumonia.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

All patents, patent applications, publications, product descriptions, and protocols are cited throughout this application, the disclosures of which are incorporated herein by reference in their entireties for all purposes.

What is claimed:

1. A pharmaceutical composition comprising ceftaroline or a prodrug thereof for treatment of a bacterial infection wherein the composition comprises from about 200 mg to about 800 mg of the ceftaroline or prodrug thereof, and an amount of the L-arginine adduct of formula I:

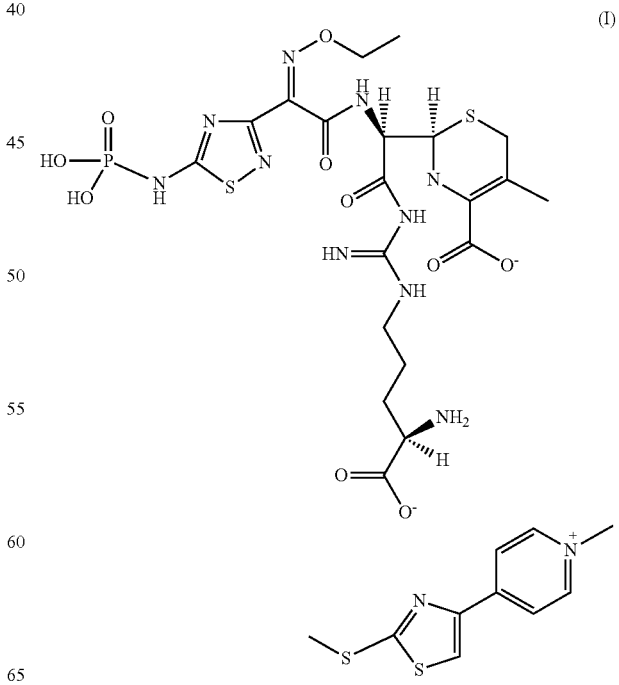

wherein said amount is less than about 2% of said pharmaceutical composition.

2. A pharmaceutical composition comprising ceftaroline or a prodrug thereof for treatment of a bacterial infection wherein the composition comprises from about 200 mg to about 800 mg of the ceftaroline or product thereof, and an amount of the L-arginine adduct of formula II:

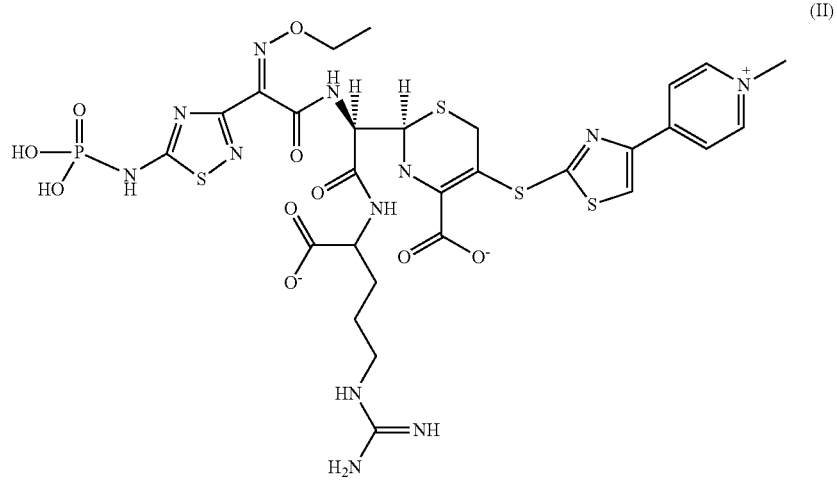

wherein said amount is less than about 2% of said pharmaceutical composition.

3. The composition of claim 1 or 2, wherein the bacterial infection is selected from the group consisting of complicated skin and skin structure infection and community-acquired bacterial pneumonia.

4. The composition of claim 1 or 2, wherein the ceftaroline or prodrug thereof is ceftaroline fosamil.

5. The composition of claim 1 or 2, wherein the bacterial infection is a complicated skin and skin structure infection.

6. The composition of claim 5, wherein the complicated skin and skin structure infection is due to a microorganism selected from the group consisting of *Staphylococcus aureus, Streptococcus pyogenes, Streptococcus agalactiae, Streptococcus dysgalactiae, Streptococcus anginosus, Streptococcus intermedius, Streptococcus constellatus, Enterococcus faecalis, Escherichia coli, Klebsiella pneumoniae, Klebsiella oxytoca* and *Morganella morganii*.

7. The composition of claim 1 or 2, wherein the bacterial infection is community-acquired bacterial pneumonia.

8. The composition of claim 7, wherein the community-acquired bacterial pneumonia is due to a microorganism selected from the group consisting of *Streptococcus pneumoniae, Staphylococcus aureus, Haemophilus influenzae, Haemophilus parainfluenzae, Klebsiella pneumoniae* and *Escherichia coli*.

* * * * *

UNITED STATES PATENT AND TRADEMARK OFFICE
CERTIFICATE OF CORRECTION

| | |
|---|---|
| PATENT NO. | : 9,629,861 B2 |
| APPLICATION NO. | : 14/722495 |
| DATED | : April 25, 2017 |
| INVENTOR(S) | : Dirk Thye et al. |

It is certified that error appears in the above-identified patent and that said Letters Patent is hereby corrected as shown below:

On the Title Page

Item (56), in Column 2, under "Other Publications", Line 6, delete "mpairment" and insert -- impairment --, therefor.

Item (56), in Column 2, under "Other Publications", Line 8, delete "Certaroline" and insert --Ceftaroline --, therefor.

Item (56), in Column 2, under "Other Publications", Line 15, delete "OPening" and insert -- Opening --, therefor.

Item (56), in Column 2, under "Other Publications", Line 25, delete "Certaroline" and insert -- Ceftaroline --, therefor.

In the Specification

In Column 9, Line 6, delete "referes" and insert -- refers --, therefor.

In Column 11, Line 61, delete "AUC0-∞," and insert -- $AUC_{0-\infty}$ --, therefor.

In Column 14, Line 46, delete "Pasturella" and insert -- Pasteurella --, therefor.

In Column 15, Line 9, delete "Haemophilis," and insert -- Haemophilus, --, therefor.

In Column 22, Line 8, delete "that that" and insert -- that --, therefor.

In Column 23, Line 1, delete "phosphonocepehem" and insert -- phosphonocephem --, therefor.

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,629,861 B2

In Column 24, Line 24, Delete "(μg · h/mL)" and insert -- "(μg·h/mL) --, therefor.

In Column 30, Line 7, delete "therapy" and insert -- therapy. --, therefor.

In Column 30, Line 11, delete "ceftriaxone" and insert -- ceftriaxone. --, therefor.

In Column 30, Line 13, delete "antimicrobial" and insert -- antimicrobial. --, therefor.

In Column 30, Line 67, delete "restrictions" and insert -- restrictions. --, therefor.

In Columns 33-34, Line 62, delete "microbiologicalintent" and insert -- microbiological intent --, therefor.

In Column 35, Line 38, delete "ceftriaxone)" and insert -- ceftriaxone). --, therefor.

In Column 36, Lines 29-30, delete "The following inclusion criteria were used:"
and insert the same on Column 36, Line 30 as a new heading.

In Column 36, Line 64, delete "study" and insert -- study. --, therefor.

In Column 38, Line 6, delete "day" and insert -- day. --, therefor.

In Column 38, Line 8, delete "formula" and insert -- formula. --, therefor.

In Column 41, Line 32, delete "favorableresponses" and insert -- favorable responses --, therefor.

In Column 42, Line 34, delete "bradychardia" and insert -- bradycardia --, therefor.